US008791232B2

(12) United States Patent  
Derkx et al.

(10) Patent No.: US 8,791,232 B2
(45) Date of Patent: Jul. 29, 2014

(54) PROTEINS

(75) Inventors: Patrick Maria Franciscus Derkx, Tikøb (DK); Harm Mulder, Noordwijk (NL); Igor Nikolaev, Noordwijk (NL)

(73) Assignee: Dupont Nutrition Biosciences APS, Copenhagen (DK)

( * ) Notice: Subject to any disclaimer, the term of this patent is extended or adjusted under 35 U.S.C. 154(b) by 339 days.

(21) Appl. No.: 12/915,204

(22) Filed: Oct. 29, 2010

(65) Prior Publication Data

US 2011/0256571 A1    Oct. 20, 2011

Related U.S. Application Data

(63) Continuation-in-part of application No. PCT/IB2009/005629, filed on Apr. 30, 2009.

(60) Provisional application No. 61/099,698, filed on Sep. 24, 2008, provisional application No. 61/099,715, filed on Sep. 24, 2008, provisional application No. 61/099,667, filed on Sep. 24, 2008.

(30) Foreign Application Priority Data

Apr. 30, 2008 (GB) .................................. 0807881.8
Apr. 30, 2008 (GB) .................................. 0807882.6
Jun. 25, 2008 (GB) .................................. 0811662.6
Sep. 17, 2008 (GB) .................................. 0817077.1

(51) Int. Cl.
C07K 14/195    (2006.01)
C07K 2/00      (2006.01)

(52) U.S. Cl.
USPC .......................................... 530/324; 530/350

(58) Field of Classification Search
None
See application file for complete search history.

(56) References Cited

U.S. PATENT DOCUMENTS

| | | | |
|---|---|---|---|
| 3,817,837 A | 6/1974 | Rubernstein | |
| 3,850,752 A | 11/1974 | Schuurs | |
| 3,939,350 A | 2/1976 | Kronick | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 4,683,202 A | 7/1987 | Mullis | |
| 4,816,567 A | 3/1989 | Cabilly et al. | |
| 5,605,793 A | 2/1997 | Stemmer | |
| 5,674,707 A | 10/1997 | Hintz et al. | |
| 5,723,323 A | 3/1998 | Kauffman et al. | |
| 5,741,665 A | 4/1998 | Kato et al. | |
| 2003/0150573 A1 | 8/2003 | Anderson et al. | |

FOREIGN PATENT DOCUMENTS

| | | |
|---|---|---|
| EP | 120516 | 10/1984 |
| EP | 0238023 | 9/1987 |
| EP | 0449375 | 10/1991 |
| WO | WO9117243 | 11/1991 |
| WO | WO9218645 | 10/1992 |
| WO | WO9735956 | 10/1997 |

OTHER PUBLICATIONS

Ruohone et al., Gene 59:161-170, 1987.*
Brockmeier et al., J. Mol. Biol., 362, 3, 393-402, 2006.*
Tan et al., Prot. Eng. 15, 4, 337-345, 2002.*
Ulf Brockmeier, et al., Systematic Screening of All Signal Peptides . . . ; J. Mol. Biol. (2006) vol. 362, p. 393-402.
Takashi Shibata, et al., Purification and Molecular Characterization . . . ; J. Biosci. Bioeng. (2001) vol. 92, No. 6, p. 524-531.
Nguan Soon Tan, et al., Engineering a Novel Secretion Signal for Cross-host . . . ; Protein Engineering (2002) vol. 15, No. 4, p. 337-345.
Altschul et al., Basic Local Alignment Search Tool, J. Mol. Biol., 1990, vol. 215 p. 403-410.
An, et al., Binary Vectors, Plant Molecular Biology Manual A3 (1988), p. 1-19.
An, et al., New Cloning Vehicles for Transformation of Higher Plants, EMBO J. (1985) vol. 4, No. 2, p. 277-284.
An, et al., Transformation of Tobacco, Tomato, Potato, and *Arabidopsis thaliana* using a Binary Ti Vector System, Plant Physiol. (1986), vol. 81, p. 301-305.
Archer, et al., The Molecular Biology of Secreted Enzyme Production by Fungi, Critical Reviews in Biotechnology (1997) vol. 17, No. 4, p. 273-306.
Beaucage, et al., Deoxynucleoside Phosphoramidites—A New Class of Key Intermediates for Deoxypolynucleotide Synthesis, Tetrahedron Letters (1981) vol. 22, No. 20, p. 1859-1862.
Beggs, Transformation of Yeast by a Replicating Hybrid Plasmid, Nature (London) (1978) vol. 275, p. 104-109.
Buchi, et al., A Synthesis of Methoxatin, J. American Chemical Society (1985) vol. 107, p. 5555-5556.
Butcher, et al., Tissue Culture Methods for Plant Pathologists, eds.: D.S. Ingrams and J.P. Helgeson (1980) The Role of Tissue Culture in the Study of Crown-Gall Tumorigenesis p. 203-208.
Caruthers, et al., New Chemical Methods for Synthesizing Polynucleotides, Nucleic Acids Research Symposium Series (1980) Series No. 7, p. 215-223.
Cereghino et al., Heterologous Protein Expression in the Methylotrophic Yeast *Pichia pastoris*, FEMS Microbiology Review (2000) vol. 24, p. 45-66.
Christou, Genetic Engineering of Crop Legumes and Cereals: Current Status and Recent Advances, Agro-Food-Industry Hi-Tech, Mar./Apr. 1994, p. 17-27.
Davis, et al., Genetic and Microbiological Research Techniques for *Neurospora crassa*, Methods Enzymology (1971) vol. 17A, p. 79-143.

(Continued)

Primary Examiner — Nancy T Vogel
(74) Attorney, Agent, or Firm — Vedder Price P.C.; Thomas J. Kowalski; Deborah L. Lu

(57) ABSTRACT

An amino acid sequence is described. The amino acid may comprise a signal sequence that is SEQ ID NO. 1a (or a variant or homologue or derivative or fragment thereof) that is expressed as a fusion protein that comprises a protein of interest. The signal sequence directs secretion of the protein of interest. The protein of interest may be a heterologous protein. Secretion of the fusion protein aids purification.

6 Claims, 8 Drawing Sheets

(56) References Cited

OTHER PUBLICATIONS

Dayhoff, et al., A Model of Evolutionary Change in Proteins, In Atlas of Protein Sequence and Structure (1978) vol. 5, Sup. 3, p. 345-352. National Biomedical Research Foundation, Washington, DC.

Fraley, et al., Genetic Transformation in Higher Plants. CRC Critical Reviews in Plant Sciences (1986) vol. 4, p. 1-46.

Frame, et al., Production of Fertile Transgenic Maize Plants by Silicon Carbide Whisker-Mediated Transformation, The Plant Journal (1994) vol. 6, No. 6, p. 941-948.

Gonnet, et al., Exhaustive Matching of the Entire Protein Sequence Database, Science (1992) vol. 256, p. 1443-1445.

Henikoff, et al., Amino Acid Substitution Matrices From Protein Blocks, Proc. Natl. Acad. Sci. USA (1992) vol. 89, p. 10915-10919.

Higgins, et al., Clustal V: Improved Software for Multiple Sequence Alignment, Computer Applications in the Biosciences (CABIOS) (1992) vol. 8, No. 2, p. 189-191.

Higgins, et al. Clustal: A Package for Performing Multiple Sequence Alignment on a Microcomputer, Gene (1988) vol. 73, p. 237-244.

Hinchcliffe, et al., Yeast As a Vehicle for the Expression of Heterologous Genes, Yeasts (1993)vol. 5, 2nd edition, p. 325-356, Academic Press Ltd.

Hinnen, et al., Transformation of Yeast, Proceedings of the National Academy of Sciences of the USA (1978) vol. 75, No. 4, p. 1929-1933.

Holland, et al., Secretion of Heterologous Proteins in *Escherichia Coli*, Methods Enzymol (1990) 182:132-43.

Hollenberg, et al., Production of Recombinant Proteins by Methylotrophic Yeasts, Current Opinion in Biotechnology (1997) vol. 8, No. 5, p. 554-560.

Horn, et al., Synthesis of Oligonucleotides on Cellulose. Part II: Design and Synthetic Strategy to the Synthesis of 22 Olgodeoxynucleotides Coding for Gastric Inhibitory Polypeptides (GIP), Nucleic Acids Research Symposium Series (1980) No. 7, p. 225-232.

Horwell, The 'Peptoid' Approach to the Design of Non-Peptide, Small Molecule Agonists and Antagonists of Neuropeptides, TibTech (1995) vol. 13, p. 132-134.

Ito, et al., Transformation of Intact Yeast Cells Treated with Alkali Cations, J. Bacteriology (1983) vol. 153, p. 163-168.

Jones, et al., The Rapid Generation of Mutation Data Matrices From Protein Sequences, Computer Applied Bioscience (1992) vol. 8, No. 3, p. 275-282.

Kumazawa, et al., Levels of Pyrroloquinoline Quinone in Various Foods, Biochem. J. (1995) 307, p. 331-333.

Larkin, et al., Clustal W and Clustal X version 2.0, Bioinformatics (2007) vol. 23, No. 21, p. 2947-2948.

LaVallie, et al. Gene Fusion Expression Systems in *Escherichia Coli*, Current Opinion in Biotechnology(1995) vol. 6, p. 501-506.

Matthes et al., Simultaneous Rapid Chemical Synthesis of Over One Hundred Oligonucleotides on a Microscale, EMBO J. (1984) vol. 3, No. 4, p. 801-805.

Meyer, et al., The Use of Cassava Mosaic Virus As a Vector System for Plants, Gene (1992) 110: 213-217.

Morinaga et al., Improvement of Oligonucleotide-Directed Site-Specific Mutagenesis Using Double-Stranded Plasmid DNA, Biotechnology (1984) vol. 2, p. 636-639.

Nelson, et al., A General Method of Site-Specific Mutagenesis Using a Modification of the *Thermos aquaticus* Polymerase Chain Reaction, Analytical Biochemistry (1989) vol. 180, p. 147-151.

Potrykus I., Gene Transfer to Plants: Assessment of Published Approaches and Results, Annual Review of Plant Physiology and Plant Molecular Biology (1991) vol. 42, p. 205-225.

Punt, et al., Filamentous Fungi As Cell Factories for Heterolgous Protein Production, Trends in Biotechnology (2002) vol. 20, No. 5, p. 200-206.

Saiki, et al., Primer-Directed Enzymatic Amplification of DNA with a Thermostable DNA Polymerase, Science (1988) vol. 239, p. 487-491.

Simon, et al.,Peptoids: A Modular Approach to Drug Discovery, Proc. Natl. Acad. Sci. USA (1992) vol. 89, p. 9367-9371.

Thompson, et al., Clustal W: Improving the Sensitivity of Progressive Multiple Sequence Alignment Through Sequence Weighting, Position-Specific Gap Penalties and Weight Matrix Choice, Nucleic Acids Research (1994) vol. 22, No. 22, p. 4673-4680.

Toyama, et al., Quinohemoprotein Alcohol Dehydrogenases: Structure, Function, and Physiology, Archives of Biochemistry and Biophysics (2004) vol. 428, p. 10-21.

Trueman, Heterologous Expression in Yeast, Methods in Molecular Biology (1995) vol. 49, p. 341-354.

Turner, Vectors for genetic manipulation. In: Martinelli S.D., Kinghorn J.R.( Editors) *Aspergillus*: 50 years on. Progress in industrial microbio-logy vol. 29. Elsevier Amsterdam 1994. pp. 641-666.

\* cited by examiner

PROTEINS

RELATED APPLICATIONS AND INCORPORATION BY REFERENCE

This application is a continuation-in-part application of international patent application Serial No. PCT/IB2009/05629 filed 30 Apr. 2009, which published as PCT Publication No. WO 2009/133462 on 5 Nov. 2009, which claims benefit of UK patent application number 0807882.6 filed 30 Apr. 2008, UK patent application number 0811662.6 filed 25 Jun. 2008 and U.S. patent application Ser. No. 61/099,667 filed 24 Sep. 2008, the contents of each of which are incorporated herein by reference.

The present application also claims benefit of the subject-matter disclosed in UK patent application number 0807881.8 filed 30 Apr. 2008 and U.S. patent application Ser. No. 61/099,698 filed 24 Sep. 2008, the contents of each of which are incorporated herein by reference.

The present application also claims benefit of the subject-matter disclosed in UK patent application number 0817077.1 filed 17 Sep. 2008 and U.S. patent application Ser. No. 61/099,715 filed 24 Sep. 2008, the contents of each of which are incorporated herein by reference.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

This invention relates to proteins.

In more detail, the present invention relates to (a) an alcohol dehydrogenase enzyme (ADH) and uses thereof and (b) a signal sequence from an ADH enzyme fused directly or indirectly (i.e. operably linked) to a protein of interest to direct secretion of the protein.

BACKGROUND OF THE INVENTION

To produce recombinant proteins cost efficiently at industrial scale it is desirable to have them secreted. This allows the proteins to be accumulated extracellularly in high amounts that be easily recovered without contamination by exogenous cellular or DNA material.

There is a constant interest, driven by industrial need, to find more effective vehicles for protein secretion.

In both prokaryotes and eukaryotes, signal peptides govern the entry of virtually all proteins to the secretory pathway and thus may affect protein production levels.

A signal peptide is a short peptide chain—typically 3-60 amino acids long—that directs the post-translational transport of a protein. Signal peptides may also be called targeting signals, signal sequences, transit peptides, or localization signals.

The amino acid sequences of signal peptides direct proteins (which are synthesized in the cytosol) to certain organelles such as the nucleus, mitochondrial matrix, endoplasmic reticulum, chloroplast, apoplast and peroxisome. Some signal peptides are cleaved from the protein by signal peptidase after the proteins are transported.

Though variable in primary sequences, signal peptides are quite universal: they can function across the species and even in different organisms.

This opens up the possibility of constructing a universal expression vector that can provide a high production level of recombinant proteins secreted into culture media in a broad range of hosts.

So far, the most commonly used signal sequence in several yeast species, including *Saccharomyces cerevisiae, Hansenula polymorpha, Pichia pastoris* is one derived from the alpha factor peptide of *S. cerevisiae*.

Citation or identification of any document in this application is not an admission that such document is available as prior art to the present invention.

SUMMARY OF THE INVENTION

In a first aspect, the invention may comprise an amino acid sequence comprising (a) SEQ ID NO: 5 or a variant or homologue or derivative or fragment thereof, or (b) SEQ ID NO: 6 or a variant or homologue or derivative or fragment thereof; wherein said amino acid sequence is not SEQ ID NO. 1; preferably wherein SEQ ID NO: 6 is fused directly or indirectly (i.e. operably linked) to a protein of interest (POI), and preferably wherein the POI is not SEQ ID NO: 5. Direct fusion is when SEQ ID NO: 6 is fused to the POI and there is no spacer. An example of indirect fusion is when SEQ ID NO: 6 is fused to the POI but wherein there may be one or more amino acids separating the sequences.

In a second aspect the invention may comprise a nucleotide sequence encoding the amino acid sequence as defined herein.

In a third aspect the invention may comprise a vector comprising the nucleotide sequence as defined herein. Preferably, the vector is an expression vector.

In a fourth aspect the invention may comprise a transformed cell comprising the vector or the nucleotide sequence as defined herein.

In a fifth aspect the invention may comprise a transformed organism comprising the transformed cell or the vector or the nucleotide sequence as defined herein.

In a sixth aspect the invention may comprise a process of preparing an amino acid sequence as defined herein wherein said amino acid sequence is obtained by expressing the transformed cell or the vector or the nucleotide sequence as defined herein.

Other aspects of the present invention may include:

An amino acid sequence comprising SEQ ID NO: 6 or a variant or homologue or derivative or fragment thereof; wherein said amino acid sequence is not SEQ ID NO. 1.

An amino acid sequence comprising at its N terminal end SEQ ID NO: 6 or a variant or homologue or derivative or fragment thereof; wherein said amino acid sequence is not SEQ ID NO. 1.

An amino acid sequence wherein said amino acid sequence is a signal sequence that is capable of causing secretion from both a prokaryotic host and a eukaryotic cell of a protein of interest (POI) when directly fused or indirectly fused to said signal sequence, wherein said amino acid sequence is not SEQ ID NO. 1.

An amino acid sequence comprising SEQ ID NO: 5 or a variant or homologue or derivative or fragment thereof; wherein said amino acid sequence is not SEQ ID NO. 1.

A nucleotide sequence encoding the amino acid sequence according to the invention.

A vector comprising the nucleotide sequence according to the invention.

A transformed host cell expressing the amino acid sequence according to the invention and/or comprising the nucleotide sequence according to the invention and/or the vector according to the invention.

A process of preparing an amino acid sequence according to the invention wherein said amino acid sequence is obtained by expressing the transformed cell according to the invention or the vector according to the invention or the nucleotide sequence according to the invention.

Use of the amino acid sequence according to the invention to have the capability to secrete in both a prokaryotic cell and a eukaryotic cell a protein of interest (POI), wherein said POI is not SEQ ID NO. 1.

Use of the transformed cell according to the invention to have the capability to secrete in both a prokaryotic cell and a eukaryotic cell a protein of interest (POI), wherein said POI is not SEQ ID NO. 1.

Use of the vector according to the invention to have the capability to secrete in both a prokaryotic cell and a eukaryotic cell a protein of interest (POI), wherein said POI is not SEQ ID NO. 1.

Use of the nucleotide sequence according to the invention to have the capability to secrete in both a prokaryotic cell and a eukaryotic cell a protein of interest (POI), wherein said POI is not SEQ ID NO. 1.

A method of selecting the expression host for production of a recombinant protein of interest (POI), wherein said POI is an amino acid sequence according to the invention; the method comprising the steps of
  (i) transforming at least one prokaryotic expression host with a nucleotide sequence according to the invention or a vector according to the invention;
  (ii) cultivating the transformed cells in order to obtain a prokaryotic expression product;
  (iii) determining at least one parameter relating to said prokaryotic expression product;
  (iv) transforming at least one eukaryotic expression host with a nucleotide sequence according to the invention or a vector according to the invention;
  (v) cultivating the transformed cells in order to obtain the eukaryotic expression product;
  (vi) determining at least one parameter relating to said eukaryotic expression product;
  (vii) comparing the parameter for the prokaryotic expression product with the parameter for the eukaryotic expression product; and
  (viii) selecting the expression host that gives the most favourable characteristic for said parameter.

In this method, the protein may be produced recombinantly for many different purposes.

The parameter may be any suitable parameter of interest—such as purity and/or yield and/or activity and/or secondary structure.

Use of an amino acid sequence according to the invention in industry.

Use of an amino acid sequence according to the invention to treat saccharides.

Use of an amino acid sequence according to the invention as an anti-foulant.

Use of an amino acid sequence according to the invention to prepare paper.

Use of an amino acid sequence according to the invention to prepare food or feed.

For some aspects, preferably said amino acid sequence may comprise an amino acid sequence that has at least 90% identity with SEQ ID NO: 6.

For some aspects, preferably said amino acid sequence may comprise an amino acid sequence that has at least 92% or at least 93% or at least 94% or at least 95% or at least 96% or at least 97% or at least 98% or at least 99% identity to SEQ ID NO: 6.

For some aspects, preferably said amino acid sequence may be either directly fused or indirectly fused to a protein of interest (POI), wherein if the amino acid sequence is directly fused to the POI then the POI is not SEQ ID NO: 5.

For some aspects, preferably said amino acid sequence may be directly fused to the POI.

For some aspects, preferably said amino acid sequence may be indirectly fused to the POI.

For some aspects, preferably said amino acid sequence may be either directly fused or indirectly fused to the N terminal end of the POI.

For some aspects, preferably said amino acid sequence may comprise an amino acid sequence that has at least 90% identity with SEQ ID NO: 5.

For some aspects, preferably said amino acid sequence may comprise an amino acid sequence that has at least 92% or at least 93% or at least 94% or at least 95% or at least 96% or at least 97% or at least 98% or at least 99% identity to SEQ ID NO: 5.

For some aspects, preferably said amino acid sequence may be either directly fused or indirectly fused to a heterologous protein or peptide.

For some aspects, preferably said heterologous protein or peptide may be a signal sequence.

For some aspects, preferably said vector may be an expression vector.

For some aspects, preferably said vector may comprise a multiple cloning site.

For some aspects, preferably said multiple cloning site may be adjacent to the nucleotide sequence encoding SEQ ID NO: 6 or the variant or homologue or derivative or fragment thereof.

For some aspects, preferably said multiple cloning site may be adjacent to the 3' end of the nucleotide sequence encoding SEQ ID NO: 6 or the variant or homologue or derivative or fragment thereof.

For some aspects, preferably said multiple cloning site may be adjacent to the 5' end of the nucleotide sequence encoding SEQ ID NO: 6 or the variant or homologue or derivative or fragment thereof.

For some aspects, preferably said multiple cloning site may be immediately adjacent to the nucleotide sequence encoding SEQ ID NO: 6 or the variant or homologue or derivative or fragment thereof For some aspects, preferably said vector may be suitable for expression in a prokaryotic host cell or a eukaryotic host cell.

For some aspects, preferably said vector may be suitable for expression in a prokaryotic host cell and a eukaryotic host cell.

For some aspects, preferably said prokaryotic host cell may be a bacterial cell.

For some aspects, preferably said prokaryotic host cell may be a *Streptomyces* cell, a *Bacillus* cell or *Escherichia coli*.

For some aspects, preferably said prokaryotic host cell may be selected from the group consisting of *Streptomyces lividans*, *Bacillus subtilis*, *Bacillus licheniformis* and *Escherichia coli*.

For some aspects, preferably said eukaryotic host cell may be a fungal cell, such as a yeast cell or a filamentous fungal cell.

For some aspects, preferably said eukaryotic host cell may be selected from the group consisting of a *Pichia* cell, an *Aspergillus* cell, a *Trichoderma* cell, a *Hansenula* cell, or a *saccharomyces* cell.

For some aspects, preferably said eukaryotic host cell may be selected from the group consisting of *Pichia pastoris, Aspergillus niger, Aspergillus tubigensis, Trichoderma reesei, Hansenula polymorpha*.

The advantages of the present invention are explained in the application.

Some advantages include the provision of an industrially useful enzyme having the amino acid sequence presented as SEQ ID NO: 5 or a variant, homologue or derivative or fragment thereof.

Other advantages include the provision of an industrially useful signal peptide presented as SEQ ID NO: 6 or a variant, homologue or derivative or fragment thereof The signal peptide is capable of causing secretion in both prokaryotic host cells and eukaryotic host cells. This is very advantageous as the present invention essentially circumvents the need of using different vectors for different expression hosts.

In comparison to the commonly used in yeast species alpha peptide signal peptide, the signal peptide of the present invention allows for a comparably efficient secretion not only in eukaryotic host cells—such as *Pichia*—but in prokaryotic host cells—such as *Bacillus*—as well. This facilitates expression analysis of a gene of interest (GOI) in both pro-eukaryotic cells by using a universal expression shuttle vector which may contain both a yeast/fungal and bacterial promoters and terminators and a common signal peptide. Thus, it is possible to can clone a GOI once in the same vector and then evaluate the expression level in different organisms using the same vector—instead of constructing different organism-adapted vectors. This greatly simplifies the procedure and saves time.

Without wishing to be bound by theory it is to noted that from the predictions of signal peptide shown in FIGS. 1A and 1B, the cleavage site was not expected to be just before the AEPS but rather 8 amino acids more to the N-terminal of the full length sequence (=SEQ ID NO 1). Thus, the signal peptide per se, was unexpected.

Thus, Applicants have surprisingly found that a sequence derived from the *Pseudogluconobacter saccharoketogenes* PQQ-dependent alcohol dehydrogenase gene is able to drive an efficient secretion of this enzyme in several organisms including the methylotrophic yeast *P. pastoris*. In addition, this signal peptide works efficiently to secrete a heterologous protein in *Bacillus subtilis*.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1A:
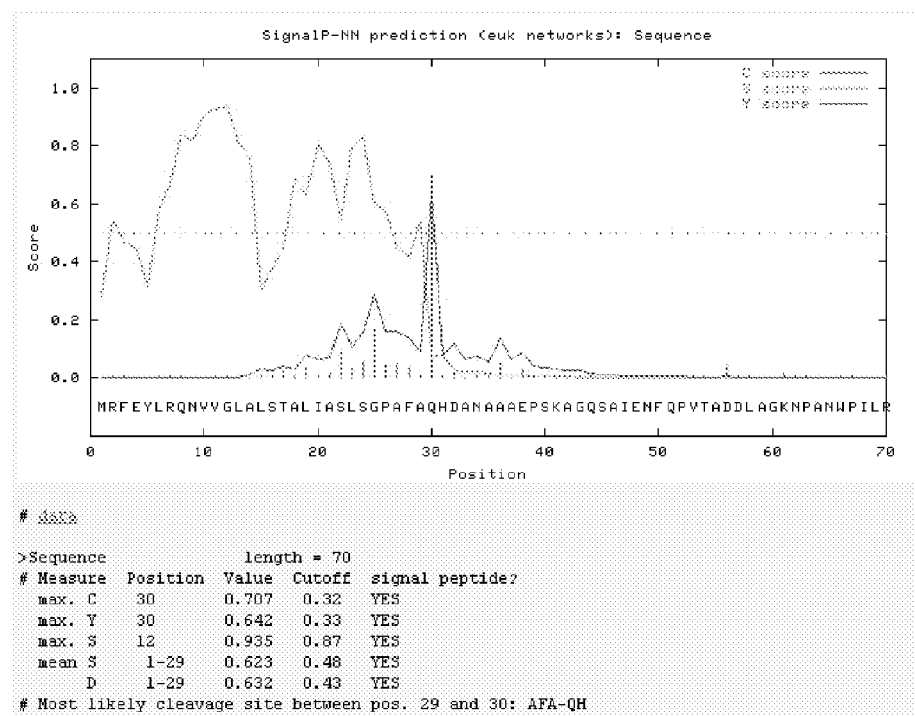
FIG. 1A. Signal peptide prediction of the *P. saccharoketogenes* PQQ-ADH in eukaryotes. Amino acid residues 1-70 of SEQ ID NO: 1 are indicated on the X-axis.

In one aspect the present invention comprises an amino acid sequence comprising SEQ ID NO: 5 or a variant or homologue or derivative or fragment thereof, or SEQ ID NO: 6 or a variant or homologue or derivative or fragment thereof; wherein said amino acid sequence is not SEQ ID NO. 1; preferably wherein SEQ ID NO: 6 is fused directly or indirectly (i.e. operably linked) to a protein of interest (POI), preferably wherein the POI is not SEQ ID NO: 5.

The scope of the present invention also encompasses amino acid sequences having the specific properties as defined herein.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

The protein used in the present invention may be used in conjunction with other proteins, particularly other enzymes, for example amylases, proteases or lipases. Thus the present invention also covers a composition comprising a combination of enzymes wherein the combination comprises the enzyme used in the present invention and another enzyme, which may be, for example, another enzyme as described herein.

Preferably the amino acid sequence when relating to and when encompassed by the per se scope of the present invention is not a native enzyme. In this regard, the term "native enzyme" means an entire enzyme that is in its native environment and when it has been expressed by its native nucleotide sequence.

In one aspect, preferably the product according to the present invention is in an isolated form. The term "isolated" means that the product is at least substantially free from at least one other component with which the product is associated in the reaction mixture.

In one aspect, preferably the product according to the present invention is in a purified form. The term "purified" means that a given component is present at a high level. The component is desirably the predominant component present in a composition. Preferably, it is present at a level of at least about 90%, or at least about 95% or at least about 98%, said level being determined on a dry weight/dry weight basis with respect to the total composition under consideration.

The scope of the present invention encompasses nucleotide sequences encoding proteins having the specific properties as defined herein.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, it may be double-stranded or single-stranded and it may represent the sense or the anti-sense strand.

The term "nucleotide sequence" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention does not include the native nucleotide sequence according to the present invention when in its natural environment and when it is linked to its naturally associated sequence(s) that is/are also in its/their natural environment. For ease of reference, Applicants shall call this preferred embodiment the "non-native nucleotide sequence".

In this regard, the term "native nucleotide sequence" means an entire nucleotide sequence that is in its native environment and when operatively linked to an entire promoter with which it is naturally associated, which promoter is also in its native environment. However, the amino acid sequence encompassed by scope the present invention can be isolated and/or purified post expression of a nucleotide sequence in its native organism. Preferably, however, the amino acid sequence encompassed by scope of the present invention may be expressed by a nucleotide sequence in its native organism but wherein the nucleotide sequence is not under the control of the promoter with which it is naturally associated within that organism.

Typically, the nucleotide sequence encompassed by the scope of the present invention is prepared using recombinant DNA techniques (i.e. recombinant DNA). However, in an alternative embodiment of the invention, the nucleotide sequence could be synthesised, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232).

A nucleotide sequence encoding either a protein which has the specific properties as defined herein or a protein which is suitable for modification may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the amino acid sequence. If the amino acid sequence is known, labelled oligonucleotide probes may be synthesised and used to identify relevant encoding clones from the genomic library prepared from the organism. Alternatively, a labelled oligonucleotide probe containing sequences homologous to another known gene could be used to identify relevant encoding clones. In the latter case, hybridisation and washing conditions of lower stringency are used.

Alternatively, relevant encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for enzyme (i.e. maltose), thereby allowing clones expressing the enzyme to be identified.

In a yet further alternative, the nucleotide sequence of the present invention may be prepared synthetically by established standard methods, e.g. the phosphoroamidite method described by Beucage S. L. et al., (1981) *Tetrahedron Letters* 22, p 1859-1869, or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science* (1988) 239, pp 487-491).

A multiple cloning site (MCS), also called a polylinker, is a short segment of DNA which contains many (usually 20+) restriction sites. Restriction sites within an MCS are typically unique (i.e. they only occur once within that particular plasmid).

In some aspects, the present invention relates to SEQ ID NO: 5 or a variant or homologue or derivative or fragment thereof, or (b) SEQ ID NO: 6 or a variant or homologue or derivative or fragment thereof. The following teachings, relate to SEQ ID NO: 5 or a variant or homologue or derivative or fragment thereof, or SEQ ID NO: 6 or a variant or homologue or derivative or fragment thereof.

Thus, the present invention also encompasses the use of sequences having a degree of sequence identity or sequence homology with amino acid sequence(s) of a parent polypeptide or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the sequence.

In the present context, a homologous sequence is taken to include an amino acid sequence which may be at least 50%, preferably at least 55%, such as at least 60%, for example at least 65%, at least 70%, at least 75%, at least 80%, at least 85%, at least 90%, at least 95%, at least 96%, at least 97%, at least 98% or at least 99%, identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 50%, preferably at least 55%, such as at least 60%, for example at least 65%, at least 70%, at least 75%, at least 80%, at least 85%, at least 90%, at least 95%, at least 96%, at least 97%, at least 98% or at least 99% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Sequence identity comparisons can be conducted by eye, or more usually, with the aid of readily available sequence comparison programs. These commercially available computer programs use complex comparison algorithms to align two or more sequences that best reflect the evolutionary events that might have led to the difference(s) between the two or more sequences. Therefore, these algorithms operate with a scoring system rewarding alignment of identical or similar amino acids and penalising the insertion of gaps, gap extensions and alignment of non-similar amino acids. The scoring system of the comparison algorithms include:

(i) assignment of a penalty score each time a gap is inserted (gap penalty score), (ii) assignment of a penalty score each time an existing gap is extended with an extra position (extension penalty score), (iii) assignment of high scores upon alignment of identical amino acids, and (iv) assignment of variable scores upon alignment of non-identical amino acids.

Most alignment programs allow the gap penalties to be modified. However, it is preferred to use the default values when using such software for sequence comparisons.

The scores given for alignment of non-identical amino acids are assigned according to a scoring matrix also called a substitution matrix. The scores provided in such substitution matrices are reflecting the fact that the likelihood of one amino acid being substituted with another during evolution varies and depends on the physical/chemical nature of the amino acid to be substituted. For example, the likelihood of a polar amino acid being substituted with another polar amino acid is higher compared to being substituted with a hydrophobic amino acid. Therefore, the scoring matrix will assign the highest score for identical amino acids, lower score for non-identical but similar amino acids and even lower score for non-identical non-similar amino acids. The most frequently used scoring matrices are the PAM matrices (Dayhoff et al. (1978), Jones et al. (1992)), the BLOSUM matrices (Henikoff and Henikoff (1992)) and the Gonnet matrix (Gonnet et al. (1992)).

Suitable computer programs for carrying out such an alignment include, but are not limited to, Vector NTI (Invitrogen Corp.) and the ClustalV, ClustalW and ClustalW2 programs (Higgins D G & Sharp P M (1988), Higgins et al. (1992), Thompson et al. (1994), Larkin et al. (2007). A selection of different alignment tools are available from the ExPASy Proteomics server at www.expasy.org. Another example of software that can perform sequence alignment is BLAST (Basic Local Alignment Search Tool), which is available from the webpage of National Center for Biotechnology Information which can currently be found at http://www.ncbi.nlm.nih.gov/ and which was firstly described in Altschul et al. (1990) J. Mol. Biol. 215; 403-410.

Once the software has produced an alignment, it is possible to calculate % similarity and % sequence identity. The software typically does this as part of the sequence comparison and generates a numerical result.

In one embodiment, it is preferred to use the ClustalW software for performing sequence alignments. Preferably, alignment with ClustalW is performed with the following parameters for pairwise alignment:

| | |
|---|---|
| Substitution matrix: | Gonnet 250 |
| Gap open penalty: | 20 |
| Gap extension penalty: | 0.2 |
| Gap end penalty: | None |

ClustalW2 is for example made available on the internet by the European Bioinformatics Institute at the EMBL-EBI webpage www.ebi.ac.uk under tools—sequence analysis—ClustalW2. Currently, the exact address of the ClustalW2 tool is www.ebi.ac.uk/Tools/clustalw2.

Thus, the present invention also encompasses the use of variants, homologues and derivatives of any amino acid sequence of a protein as defined herein, particularly those of SEQ ID NO: 5 or SEQ ID NO: 6.

The sequences, particularly those of SEQ ID NO: 5 or SEQ ID NO: 6, may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

The present invention also encompasses conservative substitution (substitution and replacement are both used herein to mean the interchange of an existing amino acid residue, with an alternative residue) that may occur i.e. like-for-like substitution such as basic for basic, acidic for acidic, polar for polar etc. Non-conservative substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Conservative substitutions that may be made are, for example within the groups of basic amino acids (Arginine, Lysine and Histidine), acidic amino acids (glutamic acid and aspartic acid), aliphatic amino acids (Alanine, Valine, Leucine, Isoleucine), polar amino acids (Glutamine, Asparagine, Serine, Threonine), aromatic amino acids (Phenylalanine, Tryptophan and Tyrosine), hydroxyl amino acids (Serine, Threonine), large amino acids (Phenylalanine and Tryptophan) and small amino acids (Glycine, Alanine).

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ϵ-amino caproic acid#, 7-amino heptanoic acid*, L-methionine sulfone*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid and L-Phe (4-benzyl)*. The notation * has been utilised for the purpose of the discussion above (relating to homologous or non-conservative substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al. (1992), Horwell D C. (1995).

In one aspect, preferably the sequence used in the present invention is in a purified form. The term "purified" means that a given component is present at a high level. The component is desirably the predominant active component present in a composition.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector.

The present invention also encompasses sequences that are complementary to the nucleic acid sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the sequences presented herein, or any derivative, fragment or derivative thereof.

The term "variant" also encompasses sequences that are complementary to sequences that are capable of hybridising to the nucleotide sequences presented herein.

Preferably, the term "variant" encompasses sequences that are complementary to sequences that are capable of hybridising under stringent conditions (e.g. 50° C. and 0.2×SSC {1×SSC=0.15 M NaCl, 0.015 M Na$_3$ citrate pH 7.0}) to the nucleotide sequences presented herein.

More preferably, the term "variant" encompasses sequences that are complementary to sequences that are capable of hybridising under high stringent conditions (e.g. 65° C. and 0.1×SSC {1×SSC=0.15 M NaCl, 0.015 M Na$_3$ citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

Also included within the scope of the present invention are polynucleotide sequences that are capable of hybridising to the nucleotide sequences presented herein under conditions of intermediate to maximal stringency.

In a preferred aspect, the present invention covers nucleotide sequences that can hybridise to the nucleotide sequence of the present invention, or the complement thereof, under stringent conditions (e.g. 50° C. and 0.2×SSC).

In a more preferred aspect, the present invention covers nucleotide sequences that can hybridise to the nucleotide sequence of the present invention, or the complement thereof, under high stringent conditions (e.g. 65° C. and 0.1×SSC).

As a non-limiting example, it is possible to produce numerous site directed or random mutations into a nucleotide sequence, either in vivo or in vitro, and to subsequently screen for improved functionality of the encoded polypeptide by various means.

In addition, mutations or natural variants of a polynucleotide sequence can be recombined with either the wildtype or other mutations or natural variants to produce new variants. Such new variants can also be screened for improved functionality of the encoded polypeptide. The production of new preferred variants can be achieved by various methods well established in the art, for example the Error Threshold Mutagenesis (PCT Publication No. WO92/18645), oligonucleotide mediated random mutagenesis (U.S. Pat. No. 5,723,323), DNA shuffling (U.S. Pat. No. 5,605,793), exo-mediated gene assembly (PCT Publication No. WO00/58517). The application of these and similar random directed molecular evolution methods allows the identification and selection of variants of the amino acid sequences of the present invention which have preferred characteristics without any prior knowledge of protein structure or function, and allows the production of non-predictable but beneficial mutations or variants. There are numerous examples of the application of molecular evolution in the art for the optimisation or alteration of activity, such examples include, but are not limited to one or more of the following:

optimised expression and/or activity in a host cell or in vitro,
  increased enzymatic activity,
  altered substrate and/or product specificity,
  increased or decreased enzymatic or structural stability,
  altered enzymatic activity/specificity in preferred environmental conditions, e.g. temperature, pH, substrate Once a protein-encoding nucleotide sequence has been isolated, or a putative protein-encoding nucleotide sequence has been identified, it may be desirable to mutate the sequence in order to prepare a protein of the present invention.

Mutations may be introduced using synthetic oligonucleotides. These oligonucleotides contain nucleotide sequences flanking the desired mutation sites.

A suitable method is disclosed in Morinaga et al., (*Biotechnology* (1984) 2, p 646-649). Another method of introducing mutations into enzyme-encoding nucleotide sequences is described in Nelson and Long (*Analytical Biochemistry* (1989), 180, p 147-151).

In one aspect the sequence for use in the present invention is a recombinant sequence—i.e. a sequence that has been prepared using recombinant DNA techniques.

These recombinant DNA techniques are within the capabilities of a person of ordinary skill in the art. Such techniques are explained in the literature, for example, J. Sambrook, E. F. Fritsch, and T. Maniatis, 1989, *Molecular Cloning: A Laboratory Manual*, Second Edition, Books 1-3, Cold Spring Harbor Laboratory Press.

In one aspect the sequence for use in the present invention is a synthetic sequence—i.e. a sequence that has been prepared by in vitro chemical or enzymatic synthesis. It includes, but is not limited to, sequences made with optimal codon usage for host organisms—such as the methylotrophic yeasts *Pichia* and *Hansenula*.

The nucleotide sequence for use in the present invention may be incorporated into a recombinant replicable vector. The vector may be used to replicate and express the nucleotide sequence, in protein form, in and/or from a compatible host cell.

Expression may be controlled using control sequences e.g. regulatory sequences.

The protein produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

The term "expression vector" means a construct capable of in vivo or in vitro expression.

Preferably, the expression vector is incorporated into the genome of a suitable host organism. The term "incorporated" preferably covers stable incorporation into the genome.

The nucleotide sequence of the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described below to provide for expression of a polypeptide of the present invention.

The choice of vector e.g. a plasmid, cosmid, or phage vector will often depend on the host cell into which it is to be introduced.

The vectors for use in the present invention may contain one or more selectable marker genes—such as a gene, which confers antibiotic resistance e.g. ampicillin, kanamycin, chloramphenicol or tetracyclin resistance. Alternatively, the selection may be accomplished by co-transformation (as described in PCT Publication No. WO91/17243).

Vectors may be used in vitro, for example for the production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the amino acid sequence of the present invention may also be achieved by the selection of heterologous regulatory regions, e.g. promoter, secretion leader and terminator regions.

Preferably, the nucleotide sequence according to the present invention is operably linked to at least a promoter.

Other promoters may even be used to direct expression of the polypeptide of the present invention.

Examples of suitable promoters for directing the transcription of the nucleotide sequence in a bacterial, fungal or yeast host are well known in the art.

The promoter can additionally include features to ensure or to increase expression in a suitable host. For example, the features can be conserved regions such as a Pribnow Box or a TATA box.

In another embodiment, a constitutive promoter may be selected to direct the expression of the desired polypeptide of the invention. Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), α-amylase (amy), amyloglucosidase (AG— from the glaA gene), acetamidase (amdS) and glyceraldehyde-3-phosphate dehydrogenase (gpd) promoters.

Examples of strong yeast promoters are those obtainable from the genes for alcohol Dehydrogenase, lactase, 3-phosphoglycerate kinase and triosephosphate isomerase.

Examples of strong bacterial promoters are the α-amylase and SP02 promoters as well as promoters from extracellular protease genes.

The term "construct"—which is synonymous with terms such as "conjugate", "cassette" and "hybrid"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct of the present invention comprises at least the nucleotide sequence of the present invention operably linked to a promoter.

The term "host cell"—in relation to the present invention includes any cell that comprises either the nucleotide sequence or an expression vector as described above and which is used in the recombinant production of a protein having the specific properties as defined herein.

Thus, a further embodiment of the present invention provides host cells transformed or transfected with a nucleotide sequence that expresses the protein of the present invention. The cells will be chosen to be compatible with the said vector and may for example be prokaryotic (for example bacterial), fungal, yeast or plant cells.

Examples of suitable bacterial host organisms are gram positive or gram negative bacterial species.

Depending on the nature of the nucleotide sequence encoding the polypeptide of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

The host cell may be a protease deficient or protease minus strain. This may for example be the protease deficient strain *Aspergillus oryzae* JaL 125 having the alkaline protease gene named "alp" deleted. This strain is described in WO97/35956.

The term "organism" in relation to the present invention includes any organism that could comprise the nucleotide sequence coding for the polypeptide according to the present invention and/or products obtained therefrom, and/or wherein a promoter can allow expression of the nucleotide sequence according to the present invention when present in the organism.

Suitable organisms may include a prokaryote, fungus, yeast or a plant.

The term "transgenic organism" in relation to the present invention includes any organism that comprises the nucleotide sequence coding for the polypeptide according to the present invention and/or the products obtained therefrom, and/or wherein a promoter can allow expression of the nucleotide sequence according to the present invention within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, the nucleotide sequence coding for the polypeptide according to the present invention, constructs according to the present invention, vectors according to the present invention, plasmids according to the present invention, cells according to the present invention, tissues according to the present invention, or the products thereof.

For example the transgenic organism may also comprise the nucleotide sequence coding for the polypeptide of the present invention under the control of a heterologous promoter.

As indicated earlier, the host organism can be a prokaryotic or a eukaryotic organism. Examples of suitable prokaryotic hosts include *E. coli* and *Bacillus subtilis*.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol* [1991] 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

A host organism may be a fungus—such as a mould. Examples of suitable such hosts include any member belonging to the genera *Thermomyces, Acremonium, Aspergillus, Penicillium, Mucor, Neurospora, Trichoderma* and the like.

In one embodiment, the host organism may be a filamentous fungus.

Transforming filamentous fungi is discussed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings which may also be utilised in transforming filamentous fungi are reviewed in U.S. Pat. No. 5,674,707.

In addition, gene expression in filamentous fungi is taught in Punt et al. (2002) Trends Biotechnol 2002 May; 20(5):200-6, Archer & Peberdy Crit. Rev Biotechnol (1997) 17(4):273-306.

The present invention encompasses the production of transgenic filamentous fungi according to the present invention prepared by use of these standard techniques.

In one aspect, the host organism can be of the genus *Aspergillus*, such as *Aspergillus niger*.

A transgenic *Aspergillus* according to the present invention can also be prepared by following, for example, the teachings of Turner G. 1994 (Vectors for genetic manipulation. In: Martinelli S. D., Kinghorn J. R. (Editors) *Aspergillus:* 50 years on. Progress in industrial microbiology vol 29. Elsevier Amsterdam 1994. pp. 641-666).

In another embodiment, the transgenic organism can be a yeast.

A review of the principles of heterologous gene expression in yeast are provided in, for example, *Methods Mol Biol* (1995), 49:341-54, and *Curr Opin Biotechnol* (1997) October; 8(5):554-60

In this regard, yeast—such as the species *Saccharomyces cerevisi* or *Pichia pastoris* (see FEMS Microbiol Rev (2000 24(1):45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", *Yeasts*, Vol 5, Anthony H Rose and J Stuart Harrison, eds, 2nd edition, Academic Press Ltd.).

For the transformation of yeast, several transformation protocols have been developed. For example, a transgenic *Saccharomyces* according to the present invention can be prepared by following the teachings of Hinnen et al., (1978, *Proceedings of the National Academy of Sciences of the USA* 75, 1929); Beggs, J D (1978, *Nature*, London, 275, 104); and Ito, H et al (1983, J Bacteriology 153, 163-168).

The transformed yeast cells may be selected using various selective markers—such as auxotrophic markers dominant antibiotic resistance markers.

A host organism suitable for the present invention may be a plant. In this respect, the basic principle in the construction of genetically modified plants is to insert genetic information in the plant genome so as to obtain a stable maintenance of the inserted genetic material. A review of the general techniques may be found in articles by Potrykus (*Annu Rev Plant Physiol*

*Plant Mol Biol* [1991] 42:205-225) and Christou (Agro-Food-Industry Hi-Tech March/April 1994 17-27).

Direct infection of plant tissues by *Agrobacterium* is a simple technique which has been widely employed and which is described in Butcher D. N. et al., (1980), *Tissue Culture Methods for Plant Pathologists*, eds.: D. S. Ingrams and J. P. Helgeson, 203-208.

Other techniques for transforming plants include ballistic transformation, the silicon whisker carbide technique (see Frame B R, Drayton P R, Bagnaall S V, Lewnau C J, Bullock W P, Wilson H M, Dunwell J M, Thompson J A & Wang K (1994) Production of fertile transgenic maize plants by silicon carbide whisker-mediated transformation, *The Plant Journal* 6: 941-948) and viral transformation techniques (e.g. see Meyer P, Heidmann I & Niedenhof I (1992) The use of cassava mosaic virus as a vector system for plants, *Gene* 110: 213-217).

Further teachings on plant transformation may be found in EP-A-0449375.

Plant cells may be grown and maintained in accordance with well-known tissue culturing methods such as by culturing the cells in a suitable culture medium supplied with the necessary growth factors such as amino acids, plant hormones, vitamins, etc.

In a further aspect, the present invention relates to a vector system which carries a nucleotide sequence or construct according to the present invention and which is capable of introducing the nucleotide sequence or construct into the genome of an organism, such as a plant. The vector system may comprise one vector, but it may comprise two vectors. In the case of two vectors, the vector system is normally referred to as a binary vector system. Binary vector systems are described in further detail in Gynheung An et al., (1980), Binary Vectors, *Plant Molecular Biology Manual* A3, 1-19.

One extensively employed system for transformation of plant cells uses the Ti plasmid from *Agrobacterium tumefaciens* or a Ri plasmid from *Agrobacterium rhizogenes* An et al., (1986), *Plant Physiol.* 81, 301-305 and Butcher D. N. et al., (1980), *Tissue Culture Methods for Plant Pathologists*, eds.: D. S. Ingrams and J. P. Helgeson, 203-208. After each introduction method of the desired promoter or construct or nucleotide sequence according to the present invention in the plants, the presence and/or insertion of further DNA sequences may be necessary. If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et al., *Crit. Rev. Plant Sci.*, 4:1-46; and An et al., *EMBO J.* (1985) 4:277-284.

Host cells transformed with the nucleotide sequence of the present invention may be cultured under conditions conducive to the production of the encoded polypeptide and which facilitate recovery of the polypeptide from the cells and/or culture medium.

The medium used to cultivate the cells may be any conventional medium suitable for growing the host cell in questions and obtaining expression of the polypeptide.

The protein produced by a recombinant cell may be displayed on the surface of the cell.

The protein may be secreted from the host cells and may conveniently be recovered from the culture medium using well-known procedures.

Often, it is desirable for the protein to be secreted from the expression host into the culture medium from where the protein may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces, Kluyveromyces* and *Hansenula*) or the α-amylase gene (*Bacillus*).

By way of example, the secretion of heterologous proteins in *E. coli* is reviewed in Methods Enzymol (1990) 182:132-43.

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Also, recombinant immunoglobulins may be produced as shown in U.S. Pat. No. 4,816,567.

The amino acid sequence for use according to the present invention may be produced as a fusion protein, for example to aid in extraction and purification. Examples of fusion protein partners include glutathione-S-transferase (GST), 6×His, GAL4 (DNA binding and/or transcriptional activation domains) and (β-galactosidase). It may also be convenient to include a proteolytic cleavage site between the fusion protein partner and the protein sequence of interest to allow removal of fusion protein sequences.

Preferably, the fusion protein will not hinder the activity of the protein sequence.

Gene fusion expression systems in *E. coli* have been reviewed in *Curr Opin Biotechnol* (1995) 6(5):501-6.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

The sequences for use according to the present invention may also be used in conjunction with one or more additional proteins of interest (POIs) or nucleotide sequences of interest (NOIs).

Non-limiting examples of POIs include: proteins or enzymes involved in starch metabolism, proteins or enzymes involved in glycogen metabolism, acetyl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, thaumatin, transferases, transport proteins, transglutaminases, xylanases, hexose oxidase (D-hexose: $O_2$-oxidoreductase, EC 1.1.3.5) or combinations thereof. The NOI may even be an antisense sequence for any of those sequences.

The POI may even be a fusion protein, for example to aid in extraction and purification.

The POI may even be fused to a secretion sequence. In one embodiment the secretion sequence may be sequence SEQ ID NO: 6

Other sequences can also facilitate secretion or increase the yield of secreted POI. Such sequences could code for chaperone proteins as for example the product of *Aspergillus niger* cyp B gene described in UK patent application 9821198.0.

The NOI may be engineered in order to alter their activity for a number of reasons, including but not limited to, alterations which modify the processing and/or expression of the expression product thereof. By way of further example, the NOI may also be modified to optimise expression in a particular host cell. Other sequence changes may be desired in order to introduce restriction enzyme recognition sites.

The NOI may include within it synthetic or modified nucleotides—such as methylphosphonate and phosphorothioate backbones.

The NOI may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule.

In one preferred embodiment of the present invention, the amino acid sequence is used for large scale applications.

Preferably the amino acid sequence is produced in a quantity of from 1 g per liter to about 2 g per liter of the total cell culture volume after cultivation of the host organism.

Preferably the amino acid sequence is produced in a quantity of from 100 mg per liter to about 900 mg per liter of the total cell culture volume after cultivation of the host organism.

Preferably the amino acid sequence is produced in a quantity of from 250 mg per liter to about 500 mg per liter of the total cell culture volume after cultivation of the host organism.

In this specification the term 'saccharide' is intended to cover all saccharides (sugars), including naturally occurring and synthetic and semi-synthetic saccharides. The term encompasses monosaccharides (i.e. saccharides that cannot be hydrolyzed into simpler sugars), disaccharides (i.e. compounds having two monosaccharide units (moieties) joined together by a glycoside bond), oligosaccharides (i.e. compounds having 3 to 10 monosaccharide units joined together by glycoside bonds in a branched or unbranched chain or a ring (optionally having a saccharide side chain). and polysaccharides. i.e. compounds having over 10 monosaccharide units joined together by a glycoside bond in a branched or unbranched chain or a ring (optionally having a saccharide side chain).

The saccharide may be bonded to other molecules, such as biomolecules, for example peptides, polypeptides/proteins (inc. enzymes), lipids and nucleic acids. However, it is preferred for the purposes of the present invention that the saccharide is formed from monosaccharide units only.

In one embodiment, the saccharide is a monosaccharide, i.e. a saccharide that cannot be hydrolyzed into a simpler sugar. The monosaccharide may have the D- or L-configuration, and may be an aldose or ketose.

In one embodiment, the monosaccharide is a hexose, examples of which include aldohexoses such as glucose, galactose, allose, altrose, mannose, gulose, idose and talose and ketohexoses such as fructose, tagatose, psicose and sorbose. Preferably, the hexose is glucose or galactose.

In another embodiment, the monosaccharide is a pentose, examples of which include aldopentoses such as ribose, arabinose, xylose and lyxose and ketopentoses such as ribulose and xylulose. Preferably, the pentose is arabinose or xylose.

In an alternative embodiment, the saccharide is a higher saccharide, i.e. a saccharide comprising more than one monosaccharide moiety joined together by glycoside bonds and which are generally hydrolysable into their constituent monosaccharides. Examples of such higher saccharides include disaccharides (2 monosaccharide moieties), oligosaccharides (3 to 10 monosaccharide moieties) and polysaccharides (more than 10 monosaccharide moieties). In this regard, the monosaccharide moieties which form the higher saccharide may be the same or different, and may each independently have the D- or L-configuration, and may each independently be aldose or ketose moieties.

The monosaccharide units which form the higher saccharide may have the same or different numbers of carbon atoms. In one embodiment, the monosaccharide moieties of the higher saccharide are hexose moieties, examples of which include aldohexoses such as glucose, galactose, allose, altrose, mannose, gulose, idose and talose and ketohexoses such as fructose, tagatose, psicose and sorbose. Preferably, the hexose moieties of such a higher saccharide are glucose moieties.

In another embodiment, the monosaccharide moieties of the higher saccharide are aldopentose moieties such as ribose, arabinose, xylose and lyxose and ketopentoses such as ribulose and xylulose. Preferably, the pentose moieties of such a higher saccharide are arabinose or xylose moieties.

The monosaccharide moieties which form the higher saccharide are joined together by glycoside bonds. When the monosaccharide moieties are hexose moieties, the glycoside bonds may be 1,4'-glycoside bonds (which may be 1,4'-α- or 1,4'-β-glycoside bonds), 1,6'-glycoside bonds (which may be 1,6'-α- or 1,6'-β-glycoside bonds), 1,2'-glycoside bonds (which may be 1,2'-α- or 1,2'-β-glycoside bonds), or 1,3'-glycoside bonds (which may be 1,3'-α- or 1,3'-β-glycoside bonds), or any combination thereof.

In one embodiment, the higher saccharide comprises 2 monosaccharide units (i.e. is a disaccharide). Examples of suitable disaccharides include lactose, maltose, cellobiose, sucrose, trehalose, isomaltulose and trehalulose.

In another embodiment, the higher saccharide comprises 3 to 10 monosaccharide units (i.e. is an oligosaccharide). The monosaccharide units may be in a chain, which may be branched or unbranched: such oligosaccharides are referred to in this specification as 'chain oligosaccharides'. Examples of such oligosaccharides include maltotriose, maltotetraose, maltopentaose, maltohexaose, maltoheptaose, cellobiose, cellotriose, cellotetraose, cellopentaose, cellohexaose and celloheptaose, as well as fructo-oligosaccharides (FOS) which consist of short chains of fructose molecules; mannanoligosaccharides, isomaltooligosaccharides, galactooligosaccharides and xylooligosaccharides.

Alternatively, the monosaccharide units which form the oligosaccharide may form a ring, which may optionally have a saccharide side chain: such oligosaccharides are referred to in this specification as 'cyclic oligosaccharides'. Typically, the ring consists of 5 to 8 monosaccharide units, preferably 6 to 8, and more preferably 6 monosaccharide units: the side chain, where present, typically consists of 1 to 4 monosaccharide units, preferably 1 or 2.

In particular, the cyclic oligosaccharide may be a cyclodextrin. Cyclodextrins (sometimes called cycloamyloses) make up a family of cyclic oligosaccharides, composed of 5 or more α-D-glucopyranoside units linked 1→4, as in amylose (a fragment of starch). The 5-membered macrocycle is not natural. Typical cyclodextrins contain a number of glucose monomers ranging from six to eight units in a ring, creating a cone shape. Particularly preferred cyclodextrins are α-cyclodextrin (6-membered sugar ring molecule), β-cyclodextrin: (7-membered sugar ring molecule) and γ-cyclodextrin (8-membered sugar ring molecule).

In another embodiment, the higher saccharide is a polysaccharide, comprising at least 10 monosaccharide units joined together by glycoside bonds. Typically such polysaccharides, comprise at least about 40, for example at least about 100, such as at least about 200, including at least about 500, for example at least about 1000, such as at least about 5000, for example about 10000, such as at least about 50000, for example about 100000, monosaccharide units.

The monosaccharide units in such a polysaccharide may be joined in a chain, which may be branched or unbranched: such polysaccharides are referred to in this specification as 'chain polysaccharides'. Alternatively, the monosaccharide units may be joined in a ring (which may have for example about 10 to about 200, preferably about 10 to about 100, more preferably about 10 to about 50, and most preferably about 10 to about 20, monosaccharide units), which may have one or more (preferably 1 or 2) side chains each comprising 1 to 6 (preferably 1 to 4, more preferably 1 or 2) monosaccharide units: such polysaccharides are referred to in this specification as 'cyclic polysaccharides'.

In some embodiments, the polysaccharide comprises from 10 to 500000 monosaccharide units. In other embodiments, the polysaccharide comprises from about 100 to about 1000 monosaccharide units. In other embodiments, the polysaccharide comprises from about 1000 to about 10000 monosaccharide units. In other embodiments, the polysaccharide comprises from about 10000 to about 100000 monosaccharide units. In some embodiments, the polysaccharide comprises from 40 to 3000, preferably about 200 to about 2500, monosaccharide units.

Examples of such polysaccharides include starch and derivatives thereof (such as cationic or anionic, oxidised or phosphated starch), amylose, amylopectin, glycogen, cellulose or a derivative thereof (such as carboxymethyl cellulose), alginic acid or a salt or derivative thereof, polydextrose, pectin, pullulan, carrageenan, locust bean gum and guar and derivatives thereof (such as cationic or anionic guar).

In one embodiment, the polysaccharide comprises starch or a derivative thereof. Starches are glucose polymers in which glucopyranose units are bonded by α-linkages. It is made up of a mixture of amylose and amylopectin. Amylose consists of a linear chain of several hundred glucose molecules linked together by 1,4'-α-glycoside linkages. In contrast amylopectin is a branched molecule made of several thousand glucose units, the main chain comprising 1,4'-α-glycoside linkages but having 1,6'-α-glycoside branches approximately every 25 glucose units.

Derivatives of starch are also oxidisable according to the present invention, provided that the derivative contains sufficient free primary hydroxyl groups for the enzyme to act upon (i.e. the starch has a degree of substitution of less than 1). Examples of suitable starches include substituted starches (eg carboxymethyl starch) and cationic, anionic, oxidised and phosphated starches.

In one embodiment, the polysaccharide comprises glycogen. Glycogen is a polysaccharide that is found in animals and is composed of a branched chain of glucose residues.

In one embodiment, the polysaccharide comprises cellulose or a derivative thereof. Cellulose is a polymer formed from several thousand glucose units bonded together by 1,4'-β-glycoside linkages. Derivatives of cellulose are known in the art, and include hydroxyalkylcelluloses such as hydroxymethylcellulose, hydroxyethyl-cellulose, hydroxypropylcellulose and hydroxypropylmethylcellulose and carboxyalkylcelluloses such as carboxymethylcellulose and carboxyethylcellulose. Derivatives of cellulose are also oxidisable according to the present invention, provided that the derivative contains sufficient free primary hydroxyl groups for the enzyme to act upon (i.e. the cellulose has a degree of substitution of less than 1).

The amino acid sequence of the present invention relating to SEQ ID NO: 5 may be present in any concentration to enable it to perform the required function. The concentration of the amino acid sequence required depends on factors such as the method of purification and the concentration of any cofactor (where present). Suitably, the amino acid sequence is present in a concentration of at least about 0.05 ppm (by weight), such as, e.g. at least about 1 ppm, at least about 10 ppm, at least about 100 ppm, at least about 150 ppm or at least about 200 ppm. Preferably, the amino acid sequence is present in a concentration of about 0.05-500 ppm, preferably about 0.1-200 ppm, more preferably about 0.2-100 ppm, even more preferably about 0.5-50 ppm, yet more preferably about 1-50 ppm, and most preferably about 1-10 ppm (by weight).

The amino acid sequence of the present invention relating to SEQ ID NO: 5 may be used with a redox cofactor. In this specification the term 'redox cofactor' is defined as any non-protein chemical compound that assists the enzymatic redox reaction. The cofactor may be tightly bound or loosely bound to the enzyme, or unbound.

Cofactors can be divided into two broad groups: coenzymes and prosthetic groups. Coenzymes are small organic non-protein molecules that carry chemical groups between enzymes. These molecules are not bound tightly by enzymes and are released as a normal part of the catalytic cycle. In contrast, prosthetic groups form a permanent part of the protein structure.

In one embodiment, the cofactor is nicotinamide adenine dinucleotide (NAD+) or nicotinamide adenine dinucleotide phosphate (NADP$^+$). When these compounds are used as the cofactor, the reaction typically proceeds with the reduction of NAD$^+$ or NADP$^+$ to NADH$^+$ or NADPH respectively. In this specification the terms NAD$^+$ and NADP$^+$ encompasses the redox cofactors nicotinamide adenine dinucleotide (NAD$^+$) or nicotinamide adenine dinucleotide phosphate whether in their oxidised (positively charged) form or their reduced form (usually described as NADH and NADPH).

The enzyme cofactors may be present in any concentration to enable the enzyme to perform the required function. Suitably, the NAD$^+$ or NADP$^+$ cofactor is present in a concentration of about 0.01 to about 5000 ppm by weight. More preferably, the NAD+ or NADP+ is present in a concentration of about 0.10 to about 1000 ppm by weight.

In another embodiment, the cofactor is a quinone cofactor. In this specification the term 'quinone cofactor' covers any compound including a 6-membered (saturated or partially unsaturated) ring having two carbonyl (>C=O) groups as ring substituents, and which is capable of acting as a cofactor for the amino acid sequence. 1,4-quinones and 1,2-quinones, for example those of the general formulae below (wherein the wavy bonds represent attachments to the remainder of the molecule, including molecules wherein two bonds together with the carbon atoms to which they are attached form a ring) are preferred. Quinone cofactors are particularly preferred for the amino acid sequence.

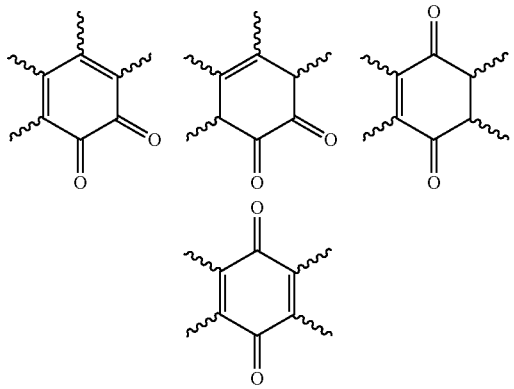

Preferably, the quinone cofactor is selected from pyrroloquinoline quinone (PQQ), tryptophyl tryptophanquinone (TTQ), topaquinone (TPQ), and lysine tyrosylquinone (LTQ), the structures of which are set out below, or acceptable salts, esters or other derivatives thereof.

Acceptable salts of the quinone cofactors used in the present invention include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Acceptable esters of the quinone cofactors used in the present invention, in particular PQQ, include ($C_{1-6}$)alkyl esters, halo($C_{1-6}$)alkyl esters, hydroxyl($C_{1-6}$)alkyl esters and ($C_{1-6}$) alkoxy($C_{1-6}$)alkyl esters, and benzyl esters. Other acceptable derivatives include N-oxide derivatives.

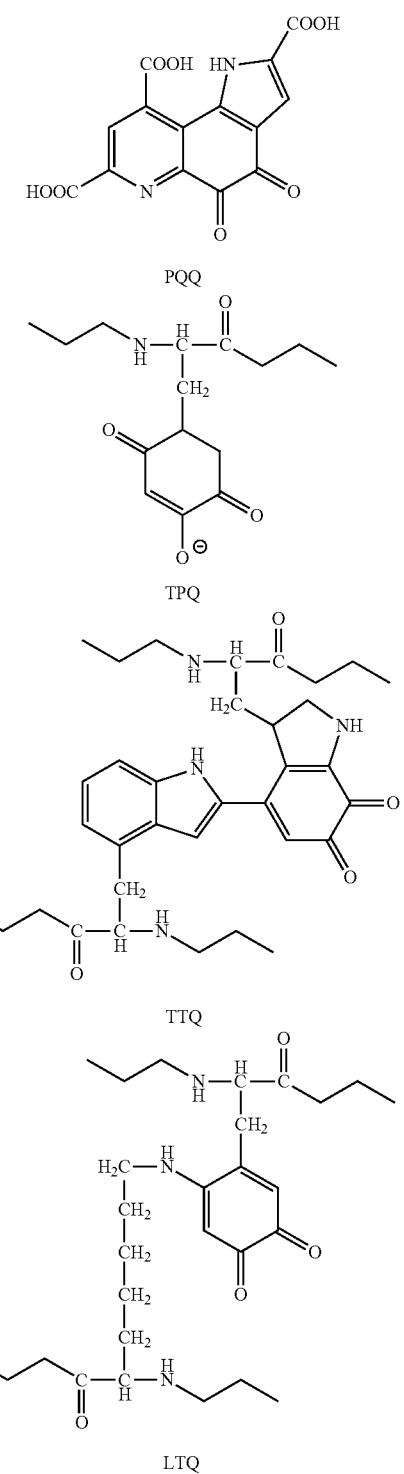

More preferably, the quinone cofactor is pyrroloquinoline quinone (PQQ) or an acceptable salt, ester or other derivative thereof. Alcohol dehydrogenase enzymes used with PQQ as cofactor are referred to in this specification as "PQQ-ADH enzymes".

When the quinone cofactor is pyrroloquinoline quinone (PQQ), the PQQ may be made synthetically, for example as described in Buchi, G., J. H. Botkin, G. C. M. Lee, and K. Yakushijin, *J. Am. Chem. Soc.* (1985) 107, 5555-5556. Alternatively, the PQQ may be obtained from natural sources, particularly foods, as described for example in Kumazawa et al., *Biochem. J.* (1995) 307, 331-333. Examples of foodstuffs containing PQQ include broad bean, green soybeans, potato, sweet potato, parsley, cabbage, carrot, celery, green pepper, spinach, tomato, apple, banana, kiwi fruit, orange, papaya, green tea, oolong (tea), cola, whiskey, wine, sake, bread, fermented soybeans (natto), miso (bean paste) and tofu (bean curd). Preferred sources of PQQ are plant extracts. A particularly preferred source of PQQ is green tea extract, as this is cheap and widely available.

When the quinone cofactor is PQQ, the PQQ is preferably present in a concentration of about 0.01 to about 1000 ppm, such as e.g., about 0.1 to about 500 ppm, about 0.15 to about 250 ppm or about 0.2 to about 100 ppm. More preferably, the PQQ is present in a concentration of about 0.25 to about 10 ppm.

When a quinone is used as cofactor with the amino acid sequence, a metal ion is preferably also used in conjunction with the amino acid sequence and quinone. Without wishing to be bound by theory, it is believed that the metal ion coordinates to the quinone and the substrate, thereby assisting transfer of hydrogen from the substrate to the quinone. Examples of suitable metal ions include alkali metal ions such as lithium, sodium and potassium ions, alkaline earth metal ions such as magnesium and calcium ions, and transition metal ions such as iron, manganese, cobalt, copper, molybdenum and zinc ions, or any combination thereof. Divalent or trivalent metal ions are preferred and calcium ions or iron ($Fe^{2+}/Fe^{3+}$) ions, or any combination thereof are particularly preferred.

According to Toyama et al, *Arch. Biochem. Biophys.* (2004) 428, 10-21, quino(hemo)protein alcohol dehydrogenases (ADH) that have pyrroloquinoline quinone (PQQ) as the cofactor group are classified into 3 groups, types I, II, and III. Type I ADH is a simple quinoprotein having PQQ as the only cofactor group, while type II and type III ADHs are quinohemoprotein having heme c as well as PQQ in the catalytic polypeptide. Type II ADH is a soluble periplasmic enzyme and is widely distributed in Proteobacteria such as *Pseudomonas, Ralstonia, Comamonas*, etc. In contrast, type III ADH is a membrane-bound enzyme working on the periplasmic surface solely in acetic acid bacteria. It consists of three subunits that comprise a quinohemoprotein catalytic subunit, a triheme cytochrome c subunit, and a third subunit of unknown function.

The amino acid sequence of the present invention (such as that relating to SEQ ID NO: 6 or SEQ ID NO: 5) has a wide range of applications.

In particular, the amino acid sequence of the present invention relating to SEQ ID NO: 5 is useful in the food and paper industries.

In one aspect, the amino acid sequence can be used to prepare modified polysaccharides useful in the paper industry. Examples of polysaccharides that are typically relevant for the paper industry include cationic, anionic, oxidized and phosphated starches; carboxymethyl cellulose (CMC), guar, alginate, guar, cationic guar and anionic guar. Further details of suitable polysaccharides may be found in US2003/150573.

Thus, in one aspect, the invention comprises a paper product including an oxidised saccharide (in particular, an oxidised polysaccharide, as defined and exemplified above) prepared by use of the amino acid sequence.

A typical paper production method may include the following steps:
(a) Chemical or mechanical pulping to produce wood pulp which helps to release cellulose
(b) Refining to process and soften the fibres
(c) Dewatering on a mesh and forming of sheets
(d) Pressing
(e) Drying
(f) Calendaring to smooth the surface
(g) Coating The above steps may be varied within the ambit of knowledge of a person skilled in the art.

For application in the food industry, at least a portion of the saccharide may be comprised in a flour. The flour may be mixed with conventional ingredients to prepare a dough. Examples of such ingredients include yeast, water, egg, milk, salt, sugar, fat and oil. The dough may then be baked to prepare a baked product.

As an alternative application in the food industry, at least a portion of the saccharide is comprised in a sugar product, for example sucrose, invert sugar, glucose, fructose or maltose.

The amino acid sequence of the present invention relating to SEQ ID NO: 5 is useful (with or without a carrier) to inhibit fouling. In particular, the amino acid sequence may be used to inhibit biofilm formation (microfouling).

Although the present invention and its advantages have been described in detail, it should be understood that various changes, substitutions and alterations can be made herein without departing from the spirit and scope of the invention as defined in the appended claims.

The present invention will now be described with reference to non-limiting examples.

EXAMPLES

The PQQ-ADH enzyme prepared in "preparation 1" is SEQ ID NO: 5.

Preparation 1: *Pseudogluconobacter saccharoketogenes* ADH

Figure 2:
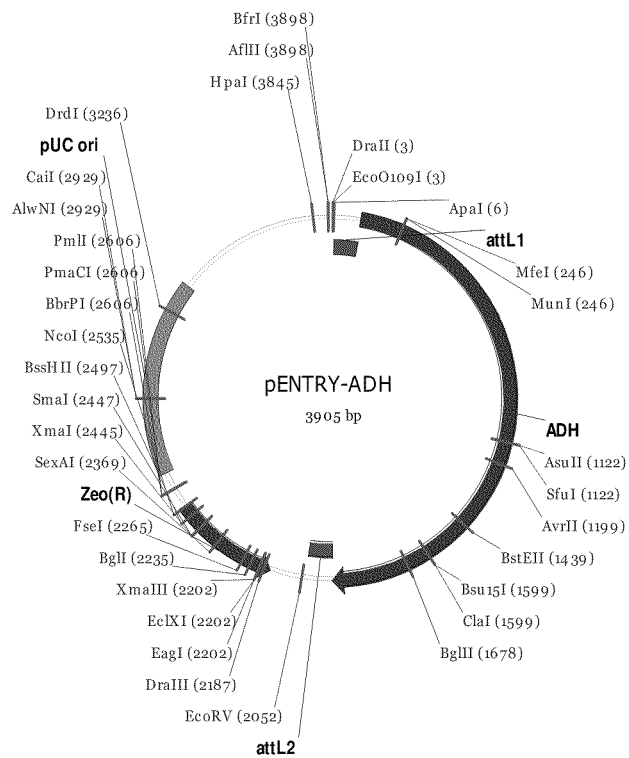
FIG. 2. Plamid map of pENTRY-ADH containing the *P. saccharoketogenes* PQQ dependent ADH gene, the Gateway compatible attL sites and the Zeocin selection marker.

The gene encoding the *Pseudogluconobacter saccharoketogenes* PQQ-dependent alcohol dehydrogenase gene (PQQ-ADH) was synthesized as a codon optimized fragment, including its own signal sequence, and cloned into the pDONR/Zeo via the Gateway® BP recombination reaction (Invitrogen, Carlsbad, Calif., USA) resulting in the entry vector pENTRY-ADH (FIG. 2). SEQ ID NO. 2 shows the DNA sequence of the codon optimized PQQ-ADH gene (from Geneart AG (Regensburg, Germany)). Shown in italics are the sequences flanking the PQQ-ADH ORF. These flanking sequences contain the attB sites that facilitate the Gateway® BP dependent cloning of the gene into pDONR/Zeo.

To enable the expression of the PQQ-ADH in *Pichia pastoris*, the gene was cloned from pENTRY-ADH into pPIC2-DEST (FIG. 3) via the Gateway® LR recombination reaction. The resulting plasmid, pPIC2-ADH (FIG. 4) was linearized by SalI digestion, enabling integration of the construct into the HIS4 locus of *P. pastoris* GS115 upon transformation. This vector contains the *P. pastoris* strong AOX1 promoter, allowing for strong methanol-inducible gene expression.

For production of PQQ-ADH, *P. pastoris*::pPIC2-ADH was grown in a 2 liter B. Braun Biostat B fermentor according to standard *P. pastoris* fermentation protocols (Invitrogen, Carlsbad, Calif. USA). During fermentation the major fraction of the expressed PQQ-ADH was found in the culture supernatant, with levels reaching 100-400 mg/l 72 hours after the start of methanol induction. The N-terminus of the mature protein was found to start at position 37 of the coding part, thus starting with AEPSKAGQSA.

The N-terminus of the PsADH expressed by *Pichia pastoris* was determined by Edman degradation and analysis on a Procise® cLC capillary 491 protein sequencing system (Applied Biosystems).

Figure 3:
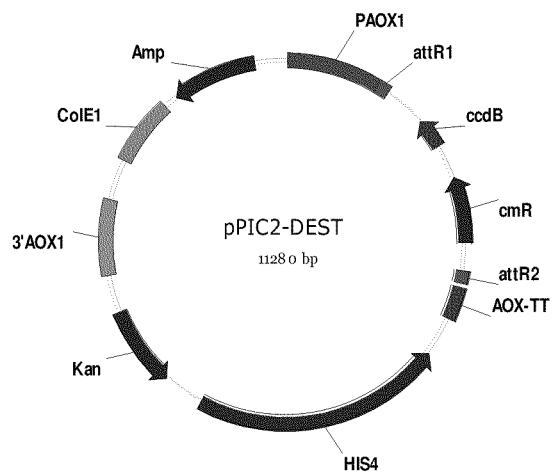
FIG. 3. Plasmid map of the *P. pastoris* destination vector pPIC2-DEST, which was derived from pPIC3.5K (Invitrogen). The vector contains the methanol inducible Gateway® cassette was inserted between promoter and terminator of pPIC3.5K, and consists of the recombination sites attR1 and 2, the chloramphenicol resistance marker (cmR) and ccdB gene for negative selection in the Gateway® cloning procedure. Furthermore, the vector contains the HIS4 gene for selection in *P. pastoris*, the kanamycin (Kan) and ampicilin (Amp) resistance genes for selection in *E. coli* (Kan).
Figure 4:
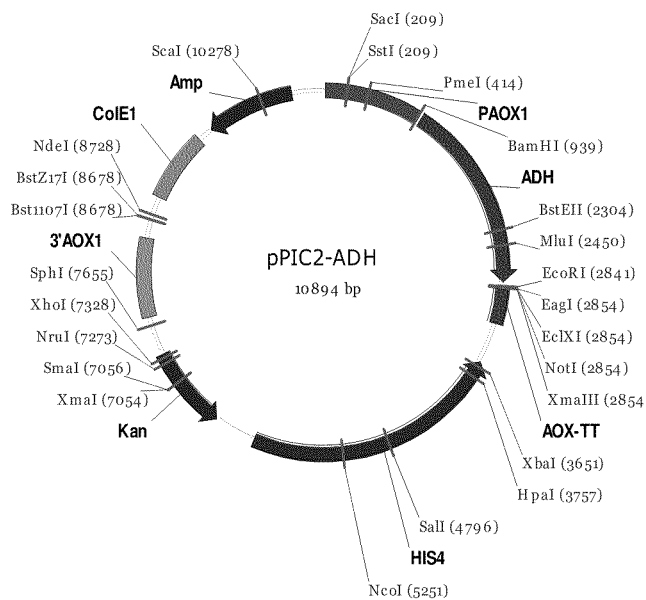
FIG. 4. Plasmid map of the *P. pastoris* PQQ-ADH expression plasmid pPIC2-ADH.

FIG. 3 is a plasmid map of the *P. pastoris* destination vector pPIC2-DEST, which was derived from pPIC3.5K (Invitrogen). The vector contains the methanol inducible A0X1 promoter (PAOX1) and the AOX transcription terminator (AOX-TT). The Gateway® cassette was inserted between promoter and terminator of pPIC3.5K, and consists of the recombination sites attR1 and 2, the chloramphenicol resistance marker (cmR) and ccdB gene for negative selection in the Gateway® cloning procedure. Furthermore, the vector contains the HIS4 gene for selection in *P. pastoris*, the kanamycin (Kan) and ampicilin (Amp) resistance genes for selection in *E. coli* (Kan).

Example I.1

Expression of the *Pseudogluconobacter saccharoketogenes* Quinoprotein Alcohol Dehydrogenase (PQQ-ADH) in Methylotrophic Yeast *Pichia pastoris*

Figure 1B:
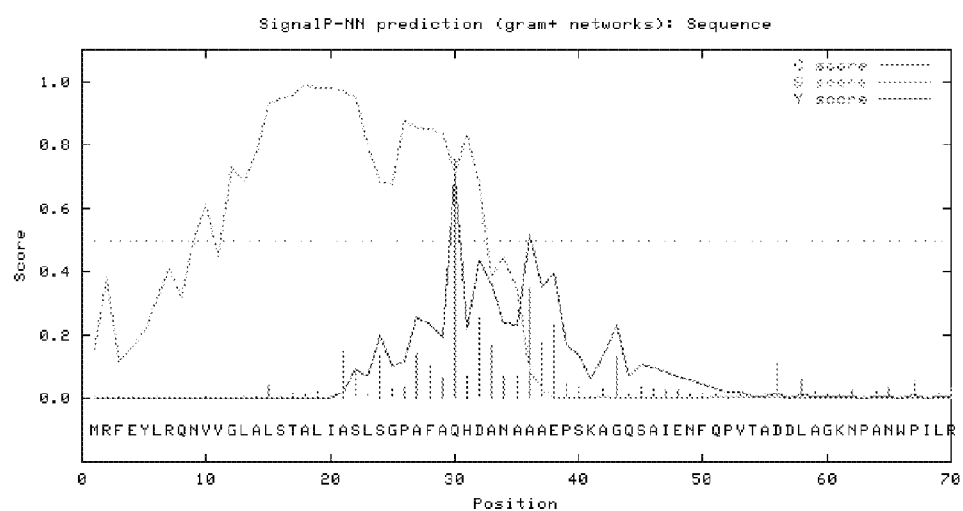
FIG. 1B. Signal peptide prediction of the *P. saccharoketogenes* PQQ-ADH in gram+ bacteria. Amino acid residues 1-70 of SEQ ID NO: 1 are indicated on the X-axis.
Figure 1C:
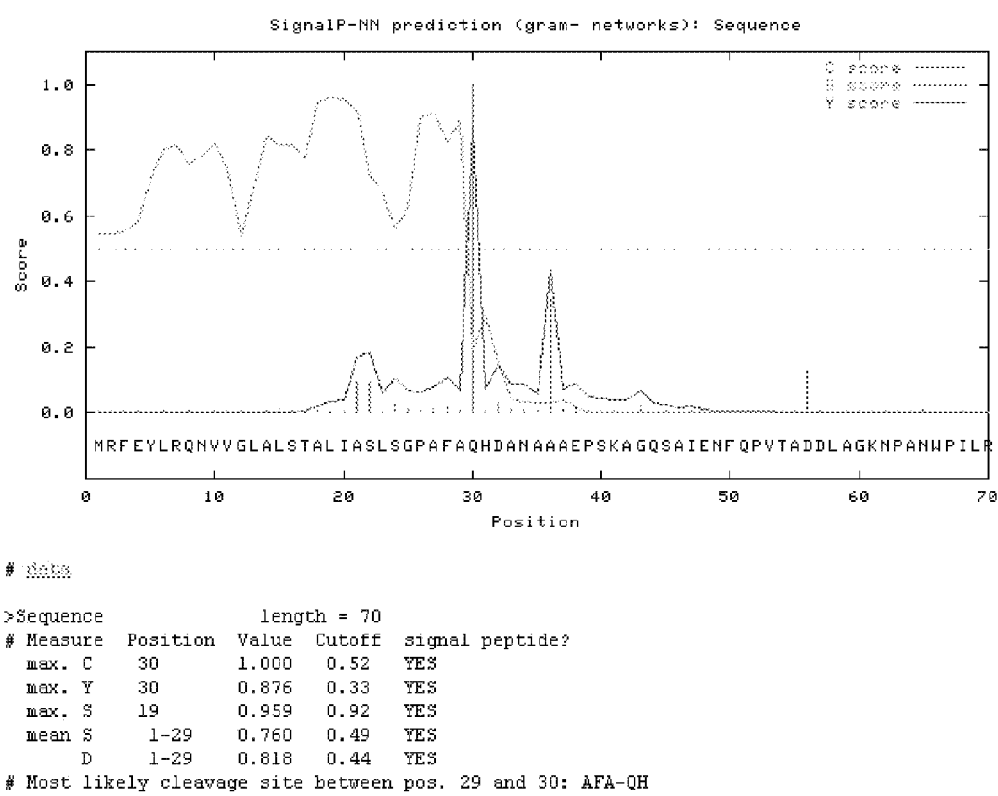
FIG. 1C. Signal peptide prediction of the *P. saccharoketogenes* PQQ-ADH in gram– bacteria. Amino acid residues 1-70 of SEQ ID NO: 1 are indicated on the X-axis.

Shibata et al. (2001) purified the quinoprotein alcohol dehydrogenase (PQQ-ADH) from *Pseudogluconobacter saccharoketogenes* from the intracellular fraction of the bacterium and published the mature sequence as such. Applicants' analysis of the published amino acid sequence using the SignalP 3.0 server (Identification of prokaryotic and eukaryotic signal peptides and prediction of their cleavage sites. Henrik Nielsen, Jacob Engelbrecht, Søren Brunak and Gunnar von Heijne. Protein Engineering, 10:1-6, 1997.) however, revealed the presence of a putative signal peptide. The prediction indicated a putative signal peptide cleavage for prokaryotes (gram+ and gram-) and eukaryotes (FIG. 1A, FIG. 1B, FIG. 1C).

To test whether the PQQ-ADH from *P. saccharoketogenes* would be secreted by *Pichia pastoris*, the gene was synthesized as a codon optimized fragment, including its own signal sequence, and cloned into the pDONR/Zeo via the Gateway® BP recombination reaction (Invitrogen, Carlsbad, Calif., USA) resulting in the entry vector pENTRY-ADH (FIG. 2). SEQ ID NO. 2 shows the DNA sequence of the codon optimized PQQ-ADH gene (from Geneart AG (Regensburg, Germany)). Shown in italics are the sequences flanking the PQQ-ADH ORF. These flanking sequences contain the attB sites that facilitate the Gateway® BP dependent cloning of the gene into pDONR/Zeo.

Figure 5A:
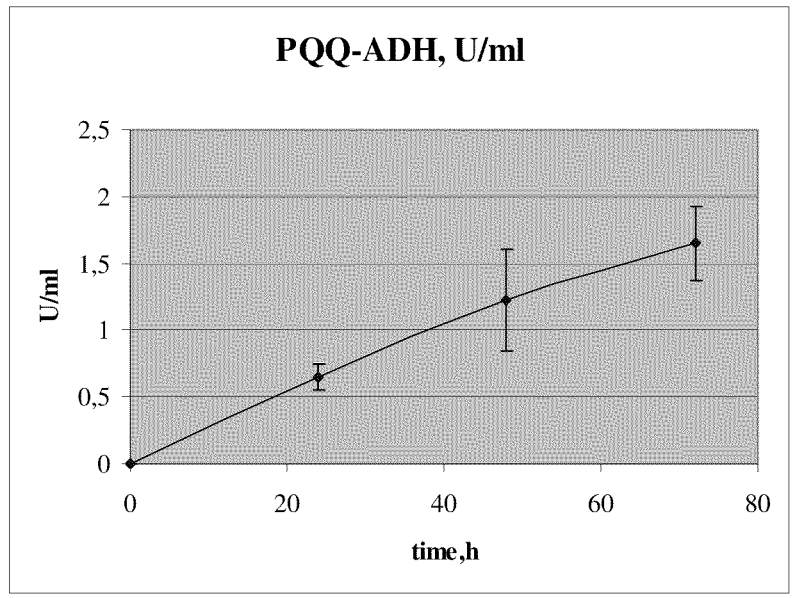
FIG. 5A. Development of extracellular PQQ-ADH activity during fermentation of *P. pastoris*::pPIC2-ADH.
Figure 5B:
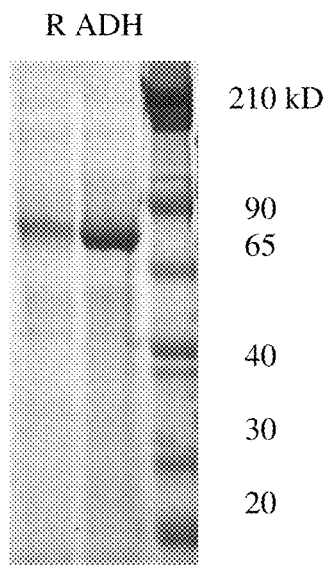
FIG. 5B. SDS-PAGE analysis of 48 h culture samples of *P. pastoris* recipient (left lane) and PQQ-ADH expressing strain (right lane).

To enable the expression of the PQQ-ADH in *Pichia pastoris*, the gene was cloned from pENTRY-ADH into pPIC2-DEST (FIG. 3) via the Gateway® LR recombination reaction. The resulting plasmid, pPIC2-ADH (FIG. 4) was linearized by SalI digestion, enabling integration of the construct into the HIS4 locus of *P. pastoris* GS115 upon transformation. This vector contains the *P. pastoris* strong AOX1 promoter, allowing for strong methanol-inducible gene expression. For production of PQQ-ADH, *P. pastoris*::pPIC2-ADH was grown in a 2 liter B. Braun Biostat B fermentor according to standard *P. pastoris* fermentation protocols (Invitrogen, Carlsbad, Calif. USA). During fermentation the major fraction of the expressed PQQ-ADH was found in the culture supernatant, with levels reaching 50-100 mg/l after 72 hours of induction with methanol (FIG. 5).

The protein was purified from the culture supernatant by Anion Exchange over a ResourceQ column. The N-terminus of the mature protein was found to start at position 37 of the coding part, thus starting with AEPSKAGQSA, which is 7 amino acids downstream of the most probable cleavage site. This protein was assayed for the activity and used in further application experiments.

Example I.2

Usage of the *P. saccharoketogenes* PQQ-ADH Signal Sequence for Efficient Secretion of the *Clostridium thermosulfurogenes* Beta-Amylase Gene Expressed in *Bacillus subtilis*

Figure 6A:
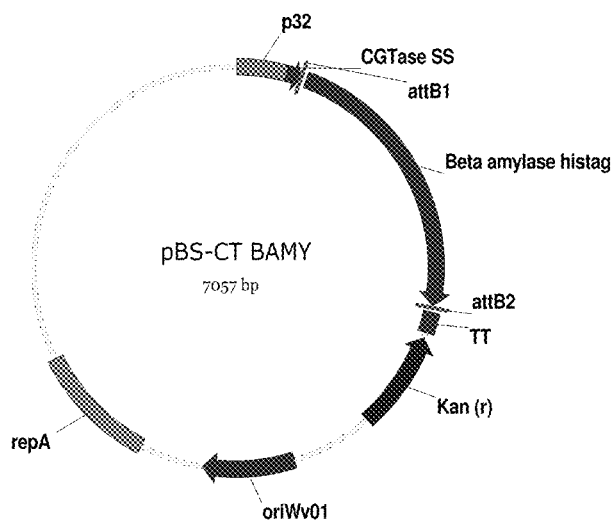
FIG. 6A. *B. subtilis* expression vector for secretion of the *C. thermosulfurogenes* beta-amylase from the cgtase signal sequence.
Figure 6B:
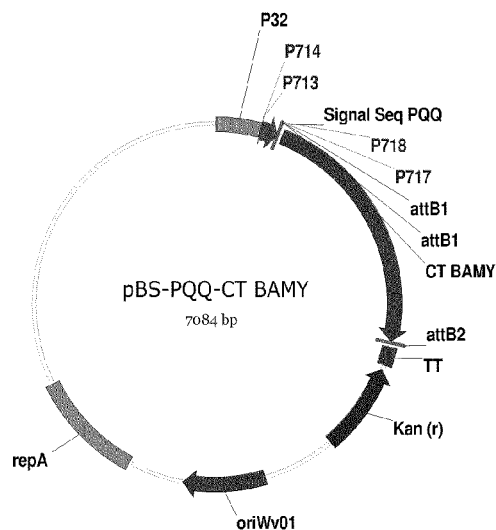
FIG. 6B. *B. subtilis* expression vector for secretion of the *C. thermosulfurogenes* beta-amylase from the PQQ-ADH signal sequence.
Figure 7:
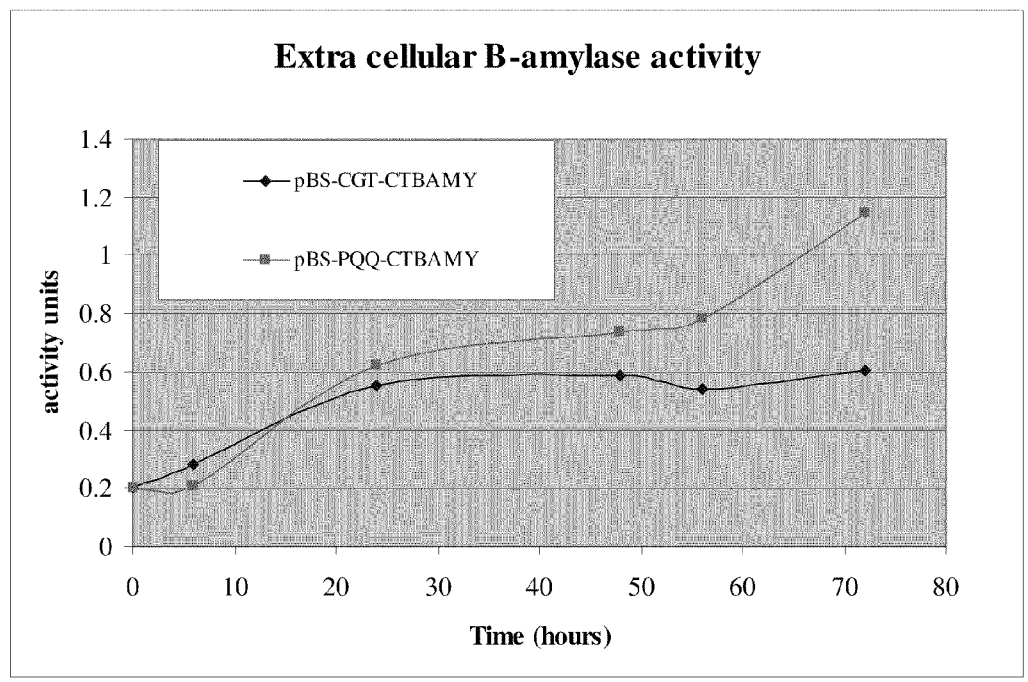
FIG. 7. Development of extracellular beta-amylase activity in the culture liquid of *B. subtilis* cells harboring either pBS-CGT-CTBAMY or pBS-PQQ-CTBAMY.

Since the PQQ-ADH was efficiently produced and secreted by eukaryotic organism *P. pastoris* despite the prokaryotic origin of the gene, Applicants tested whether the signal peptide of PQQ-ADH also would function in a prokaryotic organism. For this purpose two *Bacillus subtilis* expression vectors were constructed using standard molecular biology techniques (FIG. 6A, FIG. 6B). Both vectors are identical, except for the signal sequence that drives the secretion of the beta-amylase from *Clostridium thermosulfurogenes* which is present in both vectors (see accompanied sequences). The control vector (FIG. 6A) contains the signal sequence from the *Bacillus circulans* CGTase (pBS-CGT-CTBAMY), whereas the second vector contains the coding sequence for the first 36 amino acids of the Pseudogluconobacter saccharoketogenes PQQ-ADH (pBS-PQQ-CTBAMY). Both vectors were transformed to an amylase negative *B. subtilis* strain and the extracellular beta-amylase activity was measured using the betamyl beta-amylase kit (Megazyme) (FIG. 7). Surprisingly, the PQQ-ADH signal sequence drove the secretion of the beta-amylase even more efficiently than the *Bacillus* cgtase signal sequence. Applicants' results indicate that the first 36 amino acids of PQQ-ADH can drive protein secretion in both *P. pastoris* and *B. subtilis*

DNA sequence of the promoter region and the downstream coding region of the plasmid pBS-CGT-CTBAMY. Shown are: the P32 promoter (italics), the CGTase signal sequence (underlined), the Gateway® attB site (bold), and the beta-amylase from *Clostridium thermosulfurogenes* (normal) (SEQ ID NO. 3)

```
ggccgcggtcctcgggatatgataagattaatagttttagctattaatct ttttttattttatttaagaatggcttaataaagcggttactttggattt ttgtgagcttggactagaaaaaaacttcacaaaatgctatactaggtagg taaaaaaatattcggaggaattttgaaatggcaatcgtttcagcagaaa attcgtaattcgagctcgcccccgggatccggcgacagcggacaagcct ggaattcaaacgattacataggaggtataacatgaagaaatttctgaaat cgacagctgcgcttgccctgggattatcgctgacgttcgggcttttcagc cctgcccaggccatcacaagtttgtacaaaaaagcaggcttcggcagcat tgctcctaactttaaagtctttgtcatgggcccgcttgaaaaagtcacag attttaatgccttaaagaccaacttatcacgcttaaaaataatggtgtc tatggcattacaacggacatctggtggggctacgtcgaaaacgccggtga aaaccaatttgactggagctattataaaacatacgcggatacggtcaggg ccgcgggtcttaaatgggtccctattatgagcacgcatgcgtgcggcggc aacgtcggcgatacagtcaacatcccgattccgagctgggtctggacaaa
```

-continued

```
agatacacaagataacatgcaatacaaagacgaagcaggcaattgggaca
atgaagccgtcagcccgtggtacagcggccttacacagctttataacgaa
ttttatagcagctttgccagcaactttagcagctataaagatatcatcac
aaaaatctatattagcggcggccctagcggcgaacttaggtatcctagct
acaatccttcacatggctggacgtatcctggcaggggcagccttcagtgt
tatagcaaagcggccatcacatcatttcaaaatgcgatgaaaagcaaata
tggcacgatcgcggctgtcaatagcgcatggggtacaagccttacagatt
ttagccagattagccctcctacggacggcgataacttttttacaaacggc
tataaaacgacgtatggtaatgattttcttacatggtatcagagcgtcct
tacaaatgaacttgcgaatattgctagcgtcgctcatagctgctttgacc
cggtctttaatgtcccgattggcgcaaaaatcgcaggcgtccattggctt
tacaatagcccgacaatgccgcatgcggcagaatactgtgcgggctacta
taattatagcacgcttcttgaccaatttaaagctagcaaccttgcgatga
catttacatgccttgaaatggatgatagcaacgcctatgtcagcccgtac
tacagcgcgccgatgacacttgtccattatgtcgcaaatcttgccaataa
taaaggcattgtccataatggtgaaaatgcacttgctattagcaacaata
atcaagcgtatgtcaactgcgctaacgaacttacaggctataattttagc
ggctttacacttcttaggcttagcaacattgtcaatagcgatggcagcgt
cacaagcgaaatggcgccgtttgtcattaacatcgtcacgcttacaccga
acggcacgattcctgtcacgtttacgattaacaacgcaacaacatactat
ggccagaatgtctatcatcgtcggcagcacaagcgatcttggcaattgaa
cacgacgtatgccaggggcccggctagctgccctaattatccgacgtgga
cgatcacacttaaccttcttccgggcaacaaatccagtttaaagcggtc
aaaatcgatagcagcggcaatgtcacatgggaaggtggtagcaaccatac
atacacagtcccgacgagcggcacaggcagcgtcacaattacgtggcaaa
accaccaccaccaccactaa
```

DNA sequence of the promoter region and the downstream coding region of the plasmid pBS-PQQ-CT-BAMY. Shown are: the P32 promoter (italics), the PQQ signal sequence (underlined), the GateWay® attB site (bold), and the beta-amylase from *Clostridium thermosulfurogenes* (normal) (SEQ ID NO. 4)

```
ggccgcggtcctcgggatatgataagattaatagttttagctattaatct
ttttttatttttatttaagaatggcttaataaagcggttactttggattt
ttgtgagcttggactagaaaaaaacttcacaaaatgctatactaggtagg
taaaaaaatattcggaggaattttgaaatggcaatcgtttcagcagaaaa
attcgtaattcgagctcgcccccggggatccggcgacagcggacaagcct
ggaattcaaacgattacataggaggtataacatgagattcgagtacctgc
gccagaacgttgtcggtttggctctttctaccgccctgatcgcatccctc
agcggccctgcttttgccaacacgacgctaatgctgccatcacaagttt
gtacaaaaaagcaggcttcggcagcattgctcctaactttaaagtctttg
tcatgggcccgcttgaaaaagtcacagattttaatgccttaaagaccaa
```

-continued

```
cttatcacgcttaaaaataatggtgtctatggcattacaacggacatctg
gtggggctacgtcgaaaacgccggtgaaaaccaatttgactggagctatt
ataaaacatacgcggatacggtcagggccgcgggtctaaatgggtccct
attatgagcacgcatgcgtgcggcggcaacgtcggcgatacagtcaacat
cccgattccgagctgggtctggacaaaagatacacaagataacatgcaat
acaaagacgaagcaggcaattgggacaatgaagccgtcagcccgtggtac
agcggccttacacagctttataacgaattttatagcagctttgccagcaa
ctttagcagctataaagatatcatcacaaaaatctatattagcggcggcc
ctagcggcgaacttaggtatcctagctacaatccttcacatggctggacg
tatcctggcaggggcagccttcagtgttatagcaaagcggccatcacatc
atttcaaaatgcgatgaaaagcaaatatggcacgatcgcggctgtcaata
gcgcatggggtacaagccttacagattttagccagattagccctcctacg
gacggcgataactttttacaaacggctataaaacgacgtatggtaatga
ttttcttacatggtatcagagcgtccttacaaatgaacttgcgaatattg
ctagcgtcgctcatagctgctttgacccggtctttaatgtcccgattggc
gcaaaaatcgcaggcgtccattggctttacaatagcccgacaatgccgca
tgcggcagaatactgtgcgggctactataattatagcacgcttcttgacc
aatttaaagctagcaaccttgcgatgacatttacatgccttgaaatggat
gatagcaacgcctatgtcagcccgtactacagcgcgccgatgacacttgt
ccattatgtcgcaaatcttgccaataataaaggcattgtccataatggtg
aaaatgcacttgctattagcaacaataatcaagcgtatgtcaactgcgct
aacgaacttacaggctataattttagcggctttacacttcttaggcttag
caacattgtcaatagcgatggcagcgtcacaagcgaaatggcgccgtttg
tcattaacatcgtcacgcttacaccgaacggcacgattcctgtcacgttt
acgattaacaacgcaacaacatactatggccagaatgtctatcatcgtcgg
cagcacaagcgatcttggcaattggaacacgacgtatgccaggggcccgg
ctagctgccctaattatccgacgtggacgatcacacttaaccttcttccg
ggcgaacaaatccagtttaaagcggtcaaaatcgatagcagcggcaatgt
cacatgggaaggtggtagcaaccatacatacacagtcccgacgagcggca
caggcagcgtcacaattacgtggcaaaaccaccaccaccaccaccactaa
```

Marine Minimal Medium (MMM):

Five mL of trace element solution (1000 mg/L $FeCl_2.2H_2O$, 70 mg/L $ZnCl_2$, 80 mg/L $MnCl_2$, 6 mg/L $H_3BO_3$, 130 mg/L $CoCl_2.6H_2O$, 2 mg/L $CuCl_2.2H_2O$, 34 mg/L $NiCl_2.2H_2O$, 36 mg/L $Na_2MoO4.2H_2O$ in 50 mM HCl) and glucose to a final concentration of 10 mM was added to 1 L of Base medium (2.44 g/L $Na_2HPO_4$, 1.52 g/L $KH_2PO_4$, 0.50 g/L $(NH_4)2SO_4$, 0.20 g/L $MgSO_4.7H_2O$, 0.05 g/L $CaCl_2.2H_2O$, 29.22 g/L NaCl).

Artificial Sea Water (ASW):

24.0 g/L NaCl, 5.1 g/L $MgCl_2$, 4.0 g/L $Na_2SO_4$, 1.1 g/L $CaCl_2$, 0.67 g/L KCl, 0.098 g/L KBr, 0.027 g/L $H_3BO_3$, 0.024 g/L $SrCl_2$, 0.003 g/L NaF, 0.196 g/L $NaHCO_3$.

Phosphate Buffered Saline (PBS) pH 7.4:

137 mM NaCl, 27 mM KCl, 100 mM $Na_2HPO_4$, 2 mM $K_2HPO_4$. pH adjusted to 7.4.

Bacterial Strains:

The marine bacterium *Cobetia marina* (DSMZ 4741) was cultured in marine minimal medium pH 8.2) at 25° C. to an $OD_{600}$ of 0.8-1.0 (overnight). The cells were harvested and resuspended in ASW to an $OD_{600}$ of 0.3.

*Listeria innocua* was cultured in LB medium at 25° C. to an $OD_{600}$ of 0.8-1.0 (overnight). The cells were resuspended in PBS pH 7.4 to an $OD_{600}$ of 0.3.

Enzyme Preparations:

*Pseudogluconobacter saccharoketogenes* alcohol dehydrogenase (PsADH) (Acc BAB62258) was prepared as described above.

*Escherichia coli* ASD (EcASD) (Acc NP_415358) was prepared as described below.

*Lactobacillus kefir* ADH (LkADH) was obtained from Sigma (05643) (Acc AAP94029).

*Saccharomyces cerevisiae* ADH (ScADH) was obtained from Sigma (A3263) (Acc CAA91578).

*Thermoanaerobium brockii* ADH (TbADH) was obtained from Sigma (A8435) (Acc CAA46053).

Proteases:

Properase 1600L (Genetically modified bacterial serine endoprotease), Purafect 4000L (serine protease derived from a genetically modified strain of *Bacillus subtilis*), Protex 6L (serine protease (EC 3.4.21.62) derived from *Bacillus licheniformis*), were obtained from Genencor.

Other Enzymes:

Mannastar (mannanase EC 3.2.1.78) and Hexose oxidase (EC 1.1.3.5) were obtained from Genencor.

Co-Factors:

Pyrroloquinoline quinone (PQQ) was obtained from Sigma (D7783)

Green tea extract: Guardian, Green Tea Extract, were obtained from Danisco.

Nicotinamide Adenine Dinucleotide Phosphate ($NADP^+$) was obtained from Sigma (N0505): 15 mM $NADP^+$ solution was freshly prepared each time. $NADP^+$ was added to a final concentration of 750 µM in the assays when the tested enzyme was $NADP^+$ dependent.

Example II.1

Preparation 2: Expression of a Soluble Aldose Sugar Dehydrogenase from *Escherichia coli*

Figure 8:
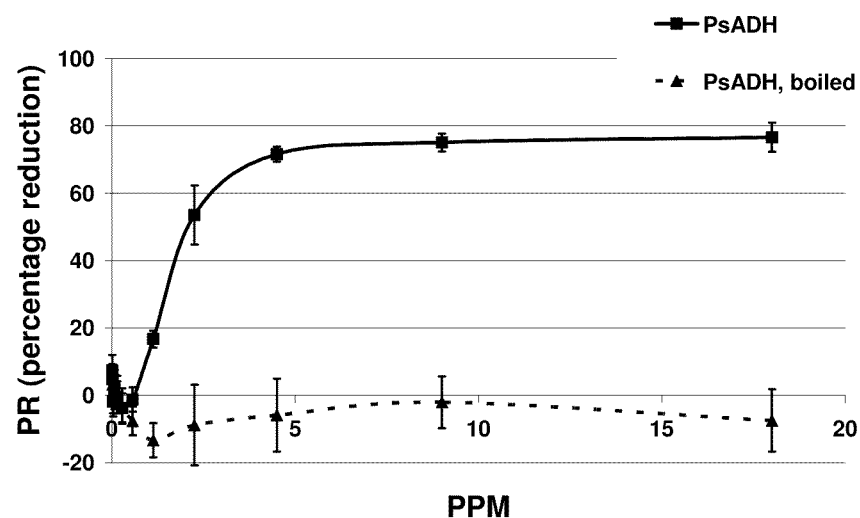
FIG. 8 is a graph illustrating the percentage reduction of biofilm formation by *Cobetia marina* plotted against concentration of *Pseudogluconobacter saccharoketogenes* ADH (PsADH).

FIG. 8 illustrates the prevention of biofilm formation by PsADH. The percentage reduction of biofilm formation by *Cobetia marina* is plotted against concentration of PsADH. Maximum inhibition is achieved at 2-5 ppm PsADH. A control experiment with boiled enzyme is shown with the dashed line.

As can be seen in FIG. 8, PsADH efficiently prevents formation of up to 90% of the biofilm formed in the absence of enzyme. The biofilm prevention activity is lost when the enzyme is heat inactivated (dashed line). The cofactor PQQ alone results in a negative PR (−24±6) indicating that it actually slightly promotes biofilm formation (data not shown).

In order to get a better understanding of the mechanism of biofilm prevention by PsADH a series of control experiments were performed. In order to exclude the hypothesis that the antifouling effect could be caused by production of hydrogen peroxide by the reaction of PsADH acting on traces of glucose or other hexoses in the medium, a control experiment was performed using hexose oxidase (HOX): if $H_2O_2$ were responsible, a similar effect would be observed when using HOX.

Figure 9:
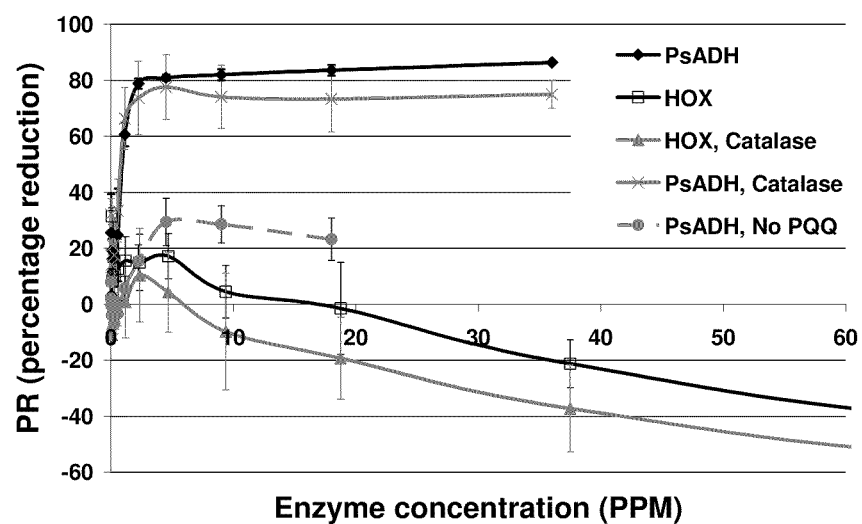
FIG. 9 is a graph illustrating the percentage reduction of biofilm formation by *Cobetia marina* plotted against the concentrations of PsADH, hexose oxidase (HOX) and HOX or PsADH in combination with catalase.

FIG. 9 illustrates the prevention of biofilm formation by PsADH, HOX and catalase. The graphs indicate the percentage reduction in biofilm formation plotted against concentration of PsADH or HOX. Catalase was included in a fixed amount of 95 ppm in combination with gradients of HOX and PsADH where indicated. Catalase was included in the assays with PsADH and HOX in order to test if the observed effect was due to production of hydrogen peroxide.

As can be seen in FIG. 9, HOX in low concentrations shows a small reduction in biofilm formation: however, at higher concentrations it promotes biofilm formation. The reduction never reaches the same efficiency as for PsADH.

As can be seen in FIG. 9, there is no significant difference in the two curves "PsADH" and "PsADH, catalase" and therefore it seems that the effect is not caused by $H_2O_2$ production.

In summary, it can be concluded that PsADH in concentrations down to 2 ppm is able to efficiently prevent biofilm formation. The effect is not due to hydrogen peroxide production since catalase cannot antagonise the effect. The PQQ cofactor is preferred for optimal effect.

Some aspects of the present invention will now be described by way of lettered paragraphs.

A. An amino acid sequence comprising (a) SEQ ID NO: 5 or a variant or homologue or derivative or fragment thereof, or (b) SEQ ID NO: 6 or a variant or homologue or derivative or fragment thereof; wherein said amino acid sequence is not SEQ ID NO. 1; preferably wherein SEQ ID NO: 6 is fused to a protein of interest (POI), wherein the POI is not SEQ ID NO: 5.

B. A nucleotide sequence encoding the amino acid sequence of paragraph A.

C. A vector comprising the nucleotide sequence of paragraph B; preferably, the vector is an expression vector.

D. A transformed cell comprising the vector of paragraph C or the nucleotide sequence of paragraph B.

E. A transformed organism comprising the transformed cell of paragraph D or the vector of paragraph 3 or the nucleotide sequence of paragraph B.

F. A process of preparing an amino acid sequence according to paragraph A wherein said amino acid sequence is obtained by expressing the transformed cell of paragraph D or the vector of paragraph C or the nucleotide sequence of paragraph B.

The invention may be further described by the following numbered paragraphs:

1. An amino acid sequence comprising SEQ ID NO: 6 or a variant or homologue or derivative or fragment thereof; wherein said amino acid sequence is not SEQ ID NO. 1.
2. An amino acid sequence according to paragraph 1 wherein said amino acid sequence comprises an amino acid sequence that has at least 90% identity with SEQ ID NO: 6.
3. An amino acid sequence according to paragraph 1 or paragraph 2 wherein said amino acid sequence comprises an amino acid sequence that has at least 92% or at least 93% or at least 94% or at least 95% or at least 96% or at least 97% or at least 98% or at least 99% identity to SEQ ID NO: 6.
4. An amino acid sequence according to any one of the preceding paragraphs wherein the amino acid sequence is either directly fused or indirectly fused to a protein of interest (POI), wherein if the amino acid sequence is directly fused to the POI then the POI is not SEQ ID NO: 5.

5. An amino acid sequence according to paragraph 4 wherein the amino acid sequence is directly fused to the POI.
6. An amino acid sequence according to paragraph 4 wherein the amino acid sequence is indirectly fused to the POI.
7. An amino acid sequence according to any one of paragraphs 4 to 6 wherein the amino acid sequence is either directly fused or indirectly fused to the N terminal end of the POI.
8. An amino acid sequence comprising at its N terminal end SEQ ID NO. 1b or a variant or homologue or derivative or fragment thereof; wherein said amino acid sequence is not SEQ ID NO. 1.
9. An amino acid sequence according to paragraph 8 wherein said amino acid sequence comprises an amino acid sequence that has at least 90% identity with SEQ ID NO: 6.
10. An amino acid sequence according to paragraph 8 or paragraph 9 wherein said amino acid sequence comprises an amino acid sequence that has at least 92% or at least 93% or at least 94% or at least 95% or at least 96% or at least 97% or at least 98% or at least 99% identity to SEQ ID NO: 6.
11. An amino acid sequence wherein said amino acid sequence is a signal sequence that is capable of causing secretion from both a prokaryotic host and a eukaryotic cell of a protein of interest (POI) when directly fused or indirectly fused to said signal sequence, wherein said amino acid sequence is not SEQ ID NO. 1.
12. An amino acid sequence according to paragraph 11 wherein said amino acid sequence is directly fused or indirectly fused to said signal sequence.
13. An amino acid sequence according to paragraph 12 wherein the amino acid sequence is directly fused to the POI.
14. An amino acid sequence according to paragraph 12 wherein the amino acid sequence is indirectly fused to the POI.
15. An amino acid sequence according to any one of paragraphs 11 to 14 wherein the amino acid sequence is either directly fused or indirectly fused to the N terminal end of the POI.
16. An amino acid sequence comprising SEQ ID NO: 5 or a variant or homologue or derivative or fragment thereof; wherein said amino acid sequence is not SEQ ID NO. 1.
17. An amino acid sequence according to paragraph 16 wherein said amino acid sequence comprises an amino acid sequence that has at least 90% identity with SEQ ID NO: 5.
18. An amino acid sequence according to paragraph 16 or paragraph 17 wherein said amino acid sequence comprises an amino acid sequence that has at least 92% or at least 93% or at least 94% or at least 95% or at least 96% or at least 97% or at least 98% or at least 99% identity to SEQ ID NO: 5.
19. An amino acid sequence according to any one of paragraphs 16 to 18 wherein the amino acid sequence is either directly fused or indirectly fused to a heterologous protein or peptide.
20. An amino acid sequence according to paragraph 19 wherein the heterologous protein or peptide is a signal sequence.
21. A nucleotide sequence encoding the amino acid sequence according to any one of paragraphs 1 to 15.
22. A vector comprising the nucleotide sequence of paragraph 21.
23. A vector according to paragraph 22 wherein the vector is an expression vector.
24. A vector according to paragraph 22 or paragraph 21 wherein said vector comprises a multiple cloning site.
25. A vector according to paragraph 24 wherein said multiple cloning site is adjacent the nucleotide sequence encoding SEQ ID NO: 6 or the variant or homologue or derivative or fragment thereof.
26. A vector according to paragraph 24 or paragraph 25 wherein said multiple cloning site is adjacent the 3' end of the nucleotide sequence encoding SEQ ID NO: 6 or the variant or homologue or derivative or fragment thereof.
27. A vector according to paragraph 24 or paragraph 25 wherein said multiple cloning site is adjacent the 5' end of the nucleotide sequence encoding SEQ ID NO: 6 or the variant or homologue or derivative or fragment thereof.
28. A vector according to any one of paragraphs 24 to 27 wherein said multiple cloning site is immediately adjacent the nucleotide sequence encoding SEQ ID NO: 6 or the variant or homologue or derivative or fragment thereof.
29. A vector according to any of paragraphs 22 to 28 wherein the vector is suitable for expression in a prokaryotic host cell or a eukaryotic host cell.
30. A vector according to any of paragraphs 22 to 29 wherein the vector is suitable for expression in a prokaryotic host cell and a eukaryotic host cell.
31. A vector according to paragraph 29 or paragraph 30 wherein the prokaryotic host cell is a bacterial cell.
32. A vector according to paragraph 31 wherein the prokaryotic host cell is a *Streptomyces* cell, a *Bacillus* cell or *Escherichia coli*.
33. A vector according to paragraph 31 wherein the prokaryotic host cell is selected from the group consisting of *Streptomyces lividans, Bacillus subtilis, Bacillus licheniformis* and *Escherichia coli*.
34. A vector according to paragraph 29 or paragraph 30 wherein the eukaryotic host cell is a fungal cell, such as a yeast cell or a filamentous fungal cell.
35. A vector according to paragraph 34 wherein the eukaryotic host cell is selected from the group consisting of a *Pichia* cell, an *Aspergillus* cell, a *Trichoderma* cell, a *Hansenula* cell, or a *saccharomyces* cell.
36. A vector according to paragraph 34 or paragraph 35 wherein the eukaryotic host cell is selected from the group consisting of *Pichia pastoris, Aspergillus niger, Aspergillus tubigensis, Trichoderma reesei,* and *Hansenula polymorpha*.
37. A transformed host cell expressing the amino acid sequence according to any one of paragraphs 1 to 15 and/or comprising the nucleotide sequence of paragraph 21 and/or the vector of any one of paragraphs 22 to 36.
38. A transformed host cell according to paragraph 37 wherein the host cell is a prokaryotic cell.
39. A transformed host cell according to paragraph 38 wherein the prokaryotic host cell is a bacterial cell.
40. A transformed host cell according to paragraph 38 or paragraph 39 wherein the prokaryotic host cell is a *Streptomyces* cell, a *Bacillus* cell or *Escherichia coli*.
41. A transformed host cell according to any one of paragraphs 38 to 40 wherein the prokaryotic host cell is 41. selected from the group consisting of *Streptomyces lividans, Bacillus subtilis, Bacillus licheniformis* and *Escherichia coli*.
42. A transformed host cell according to paragraph 37 wherein the host cell is a eukaryotic cell.
43. A transformed host cell according to paragraph 42 wherein the eukaryotic host cell is a fungal cell, such as a yeast cell or a filamentous fungal cell.
44. A transformed host cell according to paragraph 42 or 43 wherein the eukaryotic host cell is selected from the group consisting of a *Pichia* cell, an *Aspergillus* cell, a *Trichoderma* cell, a *Hansenula* cell, or a *saccharomyces* cell.
45. A transformed host cell according to any one of paragraphs 42 to 44 wherein the eukaryotic host cell is selected from the group consisting of *Pichia pastoris, Aspergillus niger, Aspergillus tubigensis, Trichoderma reesei, Hansenula polymorpha* and.
46. A process of preparing an amino acid sequence according to any one of paragraphs 1 to 15 wherein said amino acid sequence is obtained by expressing the transformed cell of any one of paragraphs 37 to 45 or the vector of any one of paragraphs 22 to 38 or the nucleotide sequence of paragraph 21.
47. Use of the amino acid sequence according to any one of paragraphs 1 to 15 to have the capability to secrete in both a prokaryotic cell and a eukaryotic cell a protein of interest (POI), wherein said POI is not SEQ ID NO. 1.
48. Use of the transformed cell of any one of paragraphs 37 to 45 to have the capability to secrete in both a prokaryotic cell and a eukaryotic cell a protein of interest (POI), wherein said POI is not SEQ ID NO. 1.
49. Use of the vector of any one of paragraphs 22 to 38 to have the capability to secrete in both a prokaryotic cell and a eukaryotic cell a protein of interest (POI), wherein said POI is not SEQ ID NO. 1.
50. Use of the nucleotide sequence of paragraph 21 to have the capability to secrete in both a prokaryotic cell and a eukaryotic cell a protein of interest (POI), wherein said POI is not SEQ ID NO. 1.
51. A method of selecting the expression host for production of a recombinant protein of interest (POI), wherein said POI is an amino acid sequence according to any one of paragraphs 1 to 15; the method comprising the steps of
    i) transforming at least one prokaryotic expression host with a nucleotide sequence according to paragraph 21 or a vector according to any one of paragraphs 22 to 36;
    ii) cultivating the transformed cells in order to obtain a prokaryotic expression product;
    iii) determining at least one parameter relating to said prokaryotic expression product;
    iv) transforming at least one eukaryotic expression host with a nucleotide sequence according to paragraph 21 or a vector according to any one of paragraphs 22 to 36;
    v) cultivating the transformed cells in order to obtain the eukaryotic expression product;
    vi) determining at least one parameter relating to said eukaryotic expression product;
    vii) comparing the parameter for the prokaryotic expression product with the parameter for the eukaryotic expression product; and
    viii) selecting the expression host that gives the most favourable characteristic for said parameter.
52. A method according to paragraph 51 wherein the prokaryotic host cell is a bacterial cell.
53. A method according to paragraph 51 or paragraph 52 wherein the prokaryotic host cell is a *Streptomyces* cell, a *Bacillus* cell or *Escherichia coli*.
54. A method according to any one of paragraphs 51 to 53 wherein the prokaryotic host cell is selected from the group consisting of *Streptomyces lividans, Bacillus subtilis, Bacillus licheniformis* and *Escherichia coli*.
55. A method according to any one of paragraphs 51 to 54 wherein the eukaryotic host cell is a fungal cell, such as a yeast cell or a filamentous fungal cell.
56. A method according to any one of paragraphs 51 to 55 wherein the eukaryotic host cell is selected from the group consisting of a *Pichia* cell, an *Aspergillus* cell, a *Trichoderma* cell, a *Hansenula* cell, or a *saccharomyces* cell.
57. A method according to any one of paragraphs 51 to 56 wherein the eukaryotic host cell is selected from the group consisting of *Pichia pastoris, Aspergillus niger, Aspergillus tubigensis, Trichoderma reesei,* and *Hansenula polymorpha.*
58. A nucleotide sequence encoding the amino acid sequence according to any one of paragraphs 16 to 20.
59. A vector comprising the nucleotide sequence of paragraph 58.
60. A vector according to paragraph 59 wherein the vector is an expression vector.
61. A vector according to paragraph 59 or paragraph 60 wherein the vector is suitable for expression in a prokaryotic host cell or a eukaryotic host cell.
62. A vector according to paragraph 61 wherein the prokaryotic host cell is a bacterial cell.
63. A vector according to paragraph 62 wherein the prokaryotic host cell is a *Streptomyces* cell, a *Bacillus* cell or *Escherichia coli*.
64. A vector according to paragraph 63 wherein the prokaryotic host cell is selected from the group consisting of *Streptomyces lividans, Bacillus subtilis, Bacillus licheniformis* and *Escherichia coli*.
65. A vector according to paragraph 59 or paragraph 60 wherein the eukaryotic host cell is a fungal cell, such as a yeast cell or a filamentous fungal cell.
66. A vector according to paragraph 65 wherein the eukaryotic host cell is selected from the group consisting of a *Pichia* cell, an *Aspergillus* cell, a *Trichoderma* cell, a *Hansenula* cell, or a *saccharomyces* cell.
67. A vector according to paragraph 65 or paragraph 66 wherein the eukaryotic host cell is selected from the group consisting of *Pichia pastoris, Aspergillus niger, Aspergillus tubigensis, Trichoderma reesei,* and *Hansenula polymorpha.*
68. A transformed host cell expressing the amino acid sequence according to any one of paragraphs 16 to 20 and/or comprising the nucleotide sequence of paragraph 58 and/or the vector of any one of paragraphs 59 to 67.
69. A transformed host cell according to paragraph 68 wherein the host cell is a prokaryotic cell.
70. A transformed host cell according to paragraph 69 wherein the prokaryotic host cell is a bacterial cell.
71. A transformed host cell according to paragraph 68 or paragraph 69 wherein the prokaryotic host cell is a *Streptomyces* cell, a *Bacillus* cell or *Escherichia coli*.
72. A transformed host cell according to any one of paragraphs 68 to 71 wherein the prokaryotic host cell is selected from the group consisting of *Streptomyces lividans, Bacillus subtilis, Bacillus licheniformis* and *Escherichia coli*.

73. A transformed host cell according to paragraph 68 wherein the host cell is a eukaryotic cell.
74. A transformed host cell according to paragraph 73 wherein the eukaryotic host cell is a fungal cell, such as a yeast cell or a filamentous fungal cell.
75. A transformed host cell according to paragraph 73 or 74 wherein the eukaryotic host cell is selected from the group consisting of a *Pichia* cell, an *Aspergillus* cell, a *Trichoderma* cell, a *Hansenula* cell, or a *saccharomyces* cell.
76. A transformed host cell according to any one of paragraphs 73 to 75 wherein the eukaryotic host cell is selected from the group consisting of *Pichia pastoris*, *Aspergillus niger*, *Aspergillus tubigensis*, *Trichoderma reesei*, and *Hansenula polymorpha*.
77. A process of preparing an amino acid sequence according to any one of paragraphs 16 to 20 wherein said amino acid sequence is obtained by expressing the transformed cell of any one of paragraphs 68 to 76 or the vector of any one of paragraphs 59 to 67 or the nucleotide sequence of paragraph 58.
78. Use of an amino acid sequence according to any one of paragraphs 16 to 20 in industry.
79. Use of an amino acid sequence according to any one of paragraphs 16 to 20 to treat saccharides.
80. Use of an amino acid sequence according to any one of paragraphs 16 to 20 as an anti-foulant.
81. Use of an amino acid sequence according to any one of paragraphs 16 to 20 to prepare paper.
82. Use of an amino acid sequence according to any one of paragraphs 16 to 20 to prepare food or feed.
83. An amino acid sequence or a nucleotide sequence or a vector or a host or a method or a use substantially as described herein and with reference to the accompanying figures.

All publications mentioned in the above specification, and references cited in said publications, are herein incorporated by reference. Various modifications and variations of the described methods and system of the present invention will be apparent to those skilled in the art without departing from the scope and spirit of the present invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

```
SEQUENCE LISTING
                                                                   SEQ ID NO. 1
Pseudogluconobacter saccharoketogenes alcohol dehydrogenase (PsADH)
EC number 1.1.5.2
(Acc BAB62258)
    1 mrfeylrqnv vglalstali aslsgpafaq hdanaaaeps kagqsaienf qpvtaddlag 61 knpanwpilr gnyqgwgysp ldqinkdnvg dlqlvwsrtm epgsnegaai ayngviflgn 121 tndviqaidg ktgsliweyr rklpsaskfi nslgaakrsi alfgdkvyfv swdnfvvald 181 aktgklawet nrgqgveegv anssgpivvd gvviagstcq fsgfgcyvtg tdaesgeelw 241 rntfiprpge egddtwggap yenrwmtgaw gqitydpeld lvyygstgag pasevqrgte 301 ggtlagtntr favkpktgev vwkhqtlprd nwdsectfem mvvstsvnpd akadgmmsvg 361 anvprgetrk vltgvpcktg vawqfdaktg dyfwskatve qnsiasiddt glvtvnedmi 421 lkepgktyny cptflggrdw psagylpksn lyviplsnac ydvmarttea tpadvyntda 481 tlvlapgktn mgrvdaidla tgetkwsyet raalydpvlt tggdlvfvgg idrdfralda 541 esgkevwstr lpgavsgytt sysidgrqyv avvsggslgg ptfgpttpdv dsasgangiy 601 vfalpekk (SEQ ID NO. 5)
Pseudogluconobacter saccharoketogenes alcohol dehydrogenase (PsADH)
EC number 1.1.5.2
(Acc BAB62258)
aeps kagqsaienf qpvtaddlag knpanwpilr gnyqgwgysp ldqinkdnvg dlqlvwsrtm epgsnegaai ayngviflgn tndviqaidg ktgsliweyr rklpsaskfi nslgaakrsi alfgdkvyfv swdnfvvald aktgklawet nrgqgveegv anssgpivvd gvviagstcq fsgfgcyvtg tdaesgeelw rntfiprpge egddtwggap yenrwmtgaw gqitydpeld lvyygstgag pasevqrgte ggtlagtntr favkpktgev vwkhqtlprd nwdsectfem mvvstsvnpd akadgmmsvg anvprgetrk vltgvpcktg vawqfdaktg dyfwskatve qnsiasiddt glvtvnedmi lkepgktyny cptflggrdw psagylpksn lyviplsnac ydvmarttea tpadvyntda tlvlapgktn mgrvdaidla tgetkwsyet raalydpvlt tggdlvfvgg idrdfralda esgkevwstr lpgavsgytt sysidgrqyv avvsggslgg ptfgpttpdv dsasgangiy
``` vfalpekk (SEQ ID NO. 6)
*Pseudogluconobacter saccharoketogenes* alcohol dehydrogenase (PsADH)
EC number 1.1.5.2
(Acc BAB62258)
  1 mrfeylrqnv vglalstali aslsgpafaq hdanaa SEQ ID NO. 2
DNA sequence of the codon optimized PQQ-ADH gene
*ggtaccacaagtttgtacaaaaaagcaggctt*catgagattcgagtacctgcgccagaacgttgtcggtt tggctctttctaccgccctgatcgcatccctcagcggccctgcttttgcccaacacgacgctaatgctgc cgccgaaccatcaaaggcaggacagtcggcaattgagaacttccaaccggtgactgctgacgatttggcc ggtaaaaaccctgcaaattggcccatccttcgtggcaactaccagggatgggggtatagtccactggacc agattaacaaggataatgtcggtgatttgcagctcgtttggtctcggacaatggaaccgggaagcaatga gggcgctgctatcgcctataacggtgtgattttctgggcaacacgaatgacgttatccaagccattgat ggaaaaaccggttcccttatctgggaatacagacgaaagctcccctcagcatctaaattcattaactcgt tggggctgctaagaggtccatcgccctgtttggcgacaaggtctacttcgtgagttgggataatttttgt tgtcgcccttgacgcaaagactggaaaactggcttgggagacaaacagaggtcaaggtgttgaggaaggc gtggccaactctagcggacctattgttgtcgatggcgtcgtgatcgcagggtccacctgccagttctcag gttttggctgttatgtgactggaacggacgctgagtcgggtgaagaattgtggcgcaataccttcattcc acgtccgggagaggaaggtgacgatacatggggcggagcaccttacgagaaccggtggatgacgggtgcc tggggccaaatcacctatgacccagaacttgatctcgtttactatggttctactggggctggacctgcct ccgaggtccagagaggtacagaaggcggcaccctggctggaactaatacacgctttgccgtgaagcccaa aacgggagaggttgtctggaaacatcaaaccttgccgagagacaactgggatagcgagtgcactttcgaa atgatggttgtctcaaccagtgtgaatccagacgctaaggcagatggtatgatgtctgttggggccaacg tgcctaggggcgagacacgtaaggttctcacgggtgtcccgtgtaaaactggcgtggcttggcagtttga tgcaaagacgggagactacttctggtcgaaagccaccgtcgaacaaaactccatcgctagcattgacgat accggtctggttacagtcaatgaggacatgattttgaaagaacccggcaagacttacaactattgcccaa cattccttggagggcgagattggccttctgccggttacctgccgaagtcaaatttgtatgtgatcccact ctccaacgcatgttacgatgttatggctagaaccactgaggccacgcccgctgacgtctataacaccgat gccacactggtgcttgcacctggcaagacgaatatgggacgcgttgacgctatcgatctcgccaccggtg aaacaaaatggtcgtacgagacaagagctgcactgtatgacccggtcttgaccactggcggagatcttgt ttttgtgggtggaattgaccgtgacttccgggctctggatgccgagagcgggaagaagtctggtctaca aggttgccaggtgcagtgtccggctacaccacgtcatacagtattgatggcagacagtatgttgccgtcg tttctggtggtagcctcggcggacctaccctttggaccgactacacccgacgtggattccgcttcgggagc aaacgggatctacgtctttgccctgcctgaaaagaagtaa*taaacccagctttcttgtacaaagtggtga*

*gctc*

SEQ ID NO. 3
DNA sequence of the promoter region and the downstream coding region
of the plasmid pBS-CGT-CTBAMY. Shown are: the P32 promoter (italics),
the CGTase signal sequence (underlined), the Gateway ® attB site
(bold), and the beta-amylase from *Clostridium thermosulfurogenes*
(normal)
*ggccgcggtcctcgggatatgataagattaatagtttttagctattaatcttttttttatttttatttaaga*

*atggcttaataaagcggttactttggattttttgtgagcttggactagaaaaaaacttcacaaaatgctat*

*actaggtaggtaaaaaaatattcggaggaattttgaaatggcaatcgtttcagcagaaaaattcgtaatt*

*cgagctcgcccccggggat*ccggcgacagcggacaagcctggaattcaaacgattacataggaggtataa

-continued catgaagaaatttctgaaatcgacagctgcgcttgccctgggattatcgctgacgttcgggcttttcagc cctgcccaggccatcacaagtttgtacaaaaaagcaggcttcggcagcattgctcctaactttaaagtct ttgtcatgggcccgcttgaaaaagtcacagattttaatgcctttaaagaccaacttatcacgcttaaaaa taatggtgtctatggcattacaacggacatctggtggggctacgtcgaaaacgccggtgaaaaccaattt gactggagctattataaaacatacgcggatacggtcagggccgcgggtcttaaatgggtccctattatga gcacgcatgcgtgcggcggcaacgtcggcgatacagtcaacatcccgattccgagctgggtctggacaaa agatacacaagataacatgcaatacaaagacgaagcaggcaattgggacaatgaagccgtcagcccgtgg tacagcggccttacacagctttataacgaattttatagcagctttgccagcaactttagcagctataaag atatcatcacaaaaatctatattagcggcggccctagcggcgaacttaggtatcctagctacaatccttc acatggctggacgtatcctggcaggggcagccttcagtgttatagcaaagcggccatcacatcatttcaa aatgcgatgaaaagcaaatatggcacgatcgcggctgtcaatagcgcatggggtacaagccttacagatt ttagccagattagccctcctacggacggcgataactttttttacaaacggctataaaacgacgtatggtaa tgattttcttacatggtatcagagcgtccttacaaatgaacttgcgaatattgctagcgtcgctcatagc tgctttgacccggtctttaatgtcccgattggcgcaaaaatcgcaggcgtccattggctttacaatagcc cgacaatgccgcatgcggcagaatactgtgcgggctactataattatagcacgcttcttgaccaatttaa agctagcaaccttgcgatgacatttacatgccttgaaatggatgatagcaacgcctatgtcagcccgtac tacagcgcgccgatgacacttgtccattatgtcgcaaatcttgccaataataaaggcattgtccataatg gtgaaaatgcacttgctattagcaacaataatcaagcgtatgtcaactgcgctaacgaacttacaggcta taattttagcggctttacacttcttaggcttagcaacattgtcaatagcgatggcagcgtcacaagcgaa atggcgccgtttgtcattaacatcgtcacgcttacaccgaacggcacgattcctgtcacgtttacgatta caacgcaacaacatactatggccagaatgtctacatcgtcggcagcacaagcgatcttggcaattggaa cacgacgtatgccaggggcccggctagctgccctaattatccgacgtggacgatcacacttaaccttctt ccgggcgaacaaatccagtttaaagcggtcaaatcgatagcagcggcaatgtcacatgggaaggtggta gcaaccatacatacacagtcccgacgagcggcacaggcagcgtcacaattacgtggcaaaaccaccaca ccaccaccactaa SEQ ID NO. 4
DNA sequence of the promoter region and the downstream coding region
of the plasmid pBS-PQQ-CT-BAMY. Shown are: the P32 promoter (italics),
the PQQ signal sequence (underlined), the GateWay ® attB site (bold),
and the beta-amylase from Clostridium thermosulfurogenes (normal)
*ggccgcggtcctcgggatatgataagattaatagttttagctattaatcttttttattttttatttaaga*

*atggcttaataaagcggttactttggattttttgtgagcttggactagaaaaaaacttcacaaaatgctat*

*actaggtaggtaaaaaaatattcggaggaattttgaaatggcaatcgtttcagcagaaaaattcgtaatt*

*cgagctcgcccccggggatccggcgacagcggacaagcctggaattcaaacgattacataggaggtataa* catgagattcgagtacctgcgccagaacgttgtcggtttggctctttctaccgccctgatcgcatccctc agcggccctgcttttgcccaacacgacgctaatgctgccatcacaagtttgtacaaaaaagcaggcttcg gcagcattgctcctaactttaaagtctttgtcatgggcccgcttgaaaaagtcacagattttaatgcctt taaagaccaacttatcacgcttaaaaataatggtgtctatggcattacaacggacatctggtggggctac gtcgaaaacgccggtgaaaaccaatttgactggagctattataaaacatacgcggatacggtcagggccg cgggtcttaaatgggtccctattatgagcacgcatgcgtgcggcggcaacgtcggcgatacagtcaacat cccgattccgagctgggtctggacaaaagatacacaagataacatgcaatacaaagacgaagcaggcaat tgggacaatgaagccgtcagcccgtggtacagcggccttacacagctttataacgaattttatagcagct ttgccagcaactttagcagctataaagatatcatcacaaaaatctatattagcggcggccctagcggcga -continued

```
acttaggtatcctagctacaatccttcacatggctggacgtatcctggcaggggcagccttcagtgttat agcaaagcggccatcacatcatttcaaaatgcgatgaaaagcaaatatggcacgatcgcggctgtcaata gcgcatggggtacaagccttacagattttagccagattagccctcctacggacggcgataacttttttac aaacggctataaaacgacgtatggtaatgattttcttacatggtatcagagcgtccttacaaatgaactt gcgaatattgctagcgtcgctcatagctgctttgacccggtctttaatgtcccgattggcgcaaaaatcg caggcgtccattggctttacaatagcccgacaatgccgcatgcggcagaatactgtgcgggctactataa ttatagcacgcttcttgaccaatttaaagctagcaaccttgcgatgacatttacatgccttgaaatggat gatagcaacgcctatgtcagcccgtactacagcgcgccgatgacacttgtccattatgtcgcaaatcttg ccaataataaaggcattgtccataatggtgaaaatgcacttgctattagcaacaataatcaagcgtatgt caactgcgctaacgaacttacaggctataattttagcggctttacacttcttaggcttagcaacattgtc aatagcgatggcagcgtcacaagcgaaatggcgccgtttgtcattaacatcgtcacgcttacaccgaacg gcacgattcctgtcacgtttacgattaacaacgcaacaacatactatggccagaatgtctacatcgtcgg cagcacaagcgatcttggcaattggaacacgacgtatgccaggggcccggctagctgccctaattatccg acgtggacgatcacacttaaccttcttccgggcgaacaaatccagtttaaagcggtcaaaatcgatagca gcggcaatgtcacatgggaaggtggtagcaaccatacatacacagtcccgacgagcggcacaggcagcgt cacaattacgtggcaaaaccaccaccaccaccactaa
```

The instant application contains a Sequence Listing which has been submitted in ASCII format via EFS-Web and is hereby incorporated by reference in its entirety.

The invention claimed is:

1. A non-naturally occurring polypeptide comprising an amino acid sequence including a signal sequence consisting of SEQ ID NO: 6; wherein said polypeptide is not SEQ ID NO: 1.

2. The polypeptide of claim 1 wherein the amino acid sequence includes a protein of interest (POI).

3. The polypeptide of claim 2 wherein the signal sequence is either directly fused or indirectly fused to the N terminal end of the POI.

4. The polypeptide of claim 1 having the signal sequence at its N terminal end.

5. The polypeptide according to claim 4 wherein the signal sequence is directly fused or indirectly fused to a protein of interest (POI).

6. The polypeptide according to claim 5 wherein the signal sequence is directly fused or indirectly fused to the N terminal end of the POI.

* * * * *

SEQUENCE LISTING

```
<160> NUMBER OF SEQ ID NOS: 9

<210> SEQ ID NO 1
<211> LENGTH: 608
<212> TYPE: PRT
<213> ORGANISM: Pseudogluconobacter saccharoketogenes

<400> SEQUENCE: 1

Met Arg Phe Glu Tyr Leu Arg Gln Asn Val Val Gly Leu Ala Leu Ser
1               5                   10                  15

Thr Ala Leu Ile Ala Ser Leu Ser Gly Pro Ala Phe Ala Gln His Asp
            20                  25                  30

Ala Asn Ala Ala Ala Glu Pro Ser Lys Ala Gly Gln Ser Ala Ile Glu
        35                  40                  45

Asn Phe Gln Pro Val Thr Ala Asp Asp Leu Ala Gly Lys Asn Pro Ala
    50                  55                  60

Asn Trp Pro Ile Leu Arg Gly Asn Tyr Gln Gly Trp Gly Tyr Ser Pro
65                  70                  75                  80

Leu Asp Gln Ile Asn Lys Asp Asn Val Gly Asp Leu Gln Leu Val Trp
                85                  90                  95

Ser Arg Thr Met Glu Pro Gly Ser Asn Glu Gly Ala Ala Ile Ala Tyr
            100                 105                 110

Asn Gly Val Ile Phe Leu Gly Asn Thr Asn Asp Val Ile Gln Ala Ile
        115                 120                 125

Asp Gly Lys Thr Gly Ser Leu Ile Trp Glu Tyr Arg Arg Lys Leu Pro
    130                 135                 140

Ser Ala Ser Lys Phe Ile Asn Ser Leu Gly Ala Ala Lys Arg Ser Ile
145                 150                 155                 160
```

-continued

```
Ala Leu Phe Gly Asp Lys Val Tyr Phe Val Ser Trp Asp Asn Phe Val
                165                 170                 175
Val Ala Leu Asp Ala Lys Thr Gly Lys Leu Ala Trp Glu Thr Asn Arg
            180                 185                 190
Gly Gln Gly Val Glu Glu Gly Val Ala Asn Ser Ser Gly Pro Ile Val
        195                 200                 205
Val Asp Gly Val Val Ile Ala Gly Ser Thr Cys Gln Phe Ser Gly Phe
    210                 215                 220
Gly Cys Tyr Val Thr Gly Thr Asp Ala Glu Ser Gly Glu Glu Leu Trp
225                 230                 235                 240
Arg Asn Thr Phe Ile Pro Arg Pro Gly Glu Glu Gly Asp Asp Thr Trp
                245                 250                 255
Gly Gly Ala Pro Tyr Glu Asn Arg Trp Met Thr Gly Ala Trp Gly Gln
            260                 265                 270
Ile Thr Tyr Asp Pro Glu Leu Asp Leu Val Tyr Tyr Gly Ser Thr Gly
        275                 280                 285
Ala Gly Pro Ala Ser Glu Val Gln Arg Gly Thr Glu Gly Gly Thr Leu
    290                 295                 300
Ala Gly Thr Asn Thr Arg Phe Ala Val Lys Pro Lys Thr Gly Glu Val
305                 310                 315                 320
Val Trp Lys His Gln Thr Leu Pro Arg Asp Asn Trp Asp Ser Glu Cys
                325                 330                 335
Thr Phe Glu Met Met Val Ser Thr Ser Val Asn Pro Asp Ala Lys
            340                 345                 350
Ala Asp Gly Met Met Ser Val Gly Ala Asn Val Pro Arg Gly Glu Thr
    355                 360                 365
Arg Lys Val Leu Thr Gly Val Pro Cys Lys Thr Gly Val Ala Trp Gln
370                 375                 380
Phe Asp Ala Lys Thr Gly Asp Tyr Phe Trp Ser Lys Ala Thr Val Glu
385                 390                 395                 400
Gln Asn Ser Ile Ala Ser Ile Asp Asp Thr Gly Leu Val Thr Val Asn
                405                 410                 415
Glu Asp Met Ile Leu Lys Glu Pro Gly Lys Thr Tyr Asn Tyr Cys Pro
            420                 425                 430
Thr Phe Leu Gly Gly Arg Asp Trp Pro Ser Ala Gly Tyr Leu Pro Lys
        435                 440                 445
Ser Asn Leu Tyr Val Ile Pro Leu Ser Asn Ala Cys Tyr Asp Val Met
    450                 455                 460
Ala Arg Thr Thr Glu Ala Thr Pro Ala Asp Val Tyr Asn Thr Asp Ala
465                 470                 475                 480
Thr Leu Val Leu Ala Pro Gly Lys Thr Asn Met Gly Arg Val Asp Ala
                485                 490                 495
Ile Asp Leu Ala Thr Gly Glu Thr Lys Trp Ser Tyr Glu Thr Arg Ala
            500                 505                 510
Ala Leu Tyr Asp Pro Val Leu Thr Gly Gly Asp Leu Val Phe Val
        515                 520                 525
Gly Gly Ile Asp Arg Asp Phe Arg Ala Leu Asp Ala Glu Ser Gly Lys
    530                 535                 540
Glu Val Trp Ser Thr Arg Leu Pro Gly Ala Val Ser Gly Tyr Thr Thr
545                 550                 555                 560
Ser Tyr Ser Ile Asp Gly Arg Gln Tyr Val Ala Val Ser Gly Gly
                565                 570                 575
Ser Leu Gly Gly Pro Thr Phe Gly Pro Thr Thr Pro Asp Val Asp Ser
```

```
                  580                 585                 590
Ala Ser Gly Ala Asn Gly Ile Tyr Val Phe Ala Leu Pro Glu Lys Lys
          595                 600                 605

<210> SEQ ID NO 2
<211> LENGTH: 1894
<212> TYPE: DNA
<213> ORGANISM: Artificial Sequence
<220> FEATURE:
<223> OTHER INFORMATION: Codon optimized PQQ-ADH gene

<400> SEQUENCE: 2
ggtaccacaa gtttgtacaa aaaagcaggc ttcatgagat tcgagtacct gcgccagaac    60
gttgtcggtt tggctctttc taccgccctg atcgcatccc tcagcggccc tgcttttgcc   120
caacacgacg ctaatgctgc cgccgaacca tcaaaggcag acagtcggc aattgagaac    180 ttccaaccgg tgactgctga cgatttggcc ggtaaaaacc ctgcaaattg gcccatcctt   240
cgtggcaact accagggatg ggggtatagt ccactggacc agattaacaa ggataatgtc   300
ggtgatttgc agctcgtttg gtctcggaca atggaaccgg aagcaatga gggcgctgct    360 atcgcctata cggtgtgat ttttctgggc aacacgaatg acgttatcca agccattgat    420
ggaaaaaccg gttcccttat ctgggaatac agacgaaagc tcccctcagc atctaaattc   480
attaactcgt tggggctgc taagaggtcc atcgccctgt ttggcgacaa ggtctacttc    540
gtgagttggg ataattttgt tgtcgccctt gacgcaaaga ctggaaaact ggcttgggag   600
acaaacagag tcaaggtgt tgaggaaggc gtggccaact tagcggacc tattgttgtc    660 gatggcgtcg tgatcgcagg gtccacctgc cagttctcag gttttggctg ttatgtgact   720 ggaacgacg ctgagtcggg tgaagaattg tggcgcaata ccttcattcc acgtccggga    780
gaggaaggtg acgatacatg gggcggagca ccttacgaga accggtggat gacgggtgcc   840
tggggccaaa tcacctatga cccagaactt gatctcgttt actatggttc tactggggct   900
ggacctgcct ccgaggtcca gagaggtaca gaaggcggca ccctggctgg aactaataca   960
cgctttgccg tgaagcccaa acgggagag gttgtctgga acatcaaac cttgccgaga   1020 gacaactggg atagcgagtg cactttcgaa atgatggttg tctcaaccag tgtgaatcca   1080
gacgctaagg cagatggtat gatgtctgtt ggggccaacg tgcctagggg cgagacacgt   1140
aaggttctca cgggtgtccc cgtgtaaaact ggcgtggctt ggcagtttga tgcaaagacg   1200
ggagactact tctggtcgaa agccaccgtc gaacaaaaact ccatcgctag cattgacgat   1260
accggtctgg ttacagtcaa tgaggacatg attttgaaag aacccggcaa gacttacaac   1320
tattgcccaa cattccttgg agggcgagat tggccttctg ccggttacct gccgaagtca   1380 aattgtatg tgatcccact ctccaacgca tgttacgatg ttatggctag aaccactgag   1440
gccacgcccg ctgacgtcta taacaccgat gccacactgg tgcttgcacc tggcaagacg   1500
aatatgggac gcgttgacgc tatcgatctc gccaccggtg aaacaaaatg gtcgtacgag   1560
acaagagctg cactgtatga cccggtcttg accactggcg gagatcttgt ttttgtgggt   1620
ggaattgacc gtgacttccg ggctctggat gccgagagcg ggaaagaagt ctggtctaca   1680
aggttgccag gtgcagtgtc cggctacacc acgtcataca gtattgatgg cagacagtat   1740
gttgccgtcg tttctggtgg tagcctcggc ggacctacct ttggaccgac tacacccgac   1800
gtggattccg cttcgggagc aaacgggatc tacgtctttg ccctgcctga aaagaagtaa   1860
taaacccagc tttcttgtac aaagtggtga gctc                              1894
```

<210> SEQ ID NO 3
<211> LENGTH: 1973
<212> TYPE: DNA
<213> ORGANISM: Artificial Sequence
<220> FEATURE:
<223> OTHER INFORMATION: Synthetic construct

<400> SEQUENCE: 3

| | | | | | |
|---|---|---|---|---|---|
| ggccgcggtc | ctcgggatat | gataagatta | atagttttag | ctattaatct | tttttttattt | 60 |
| ttatttaaga | atggcttaat | aaagcggtta | ctttggattt | ttgtgagctt | ggactagaaa | 120 |
| aaaacttcac | aaaatgctat | actaggtagg | taaaaaaata | ttcggaggaa | ttttgaaatg | 180 |
| gcaatcgttt | cagcagaaaa | attcgtaatt | cgagctcgcc | cccggggatc | cggcgacagc | 240 |
| ggacaagcct | ggaattcaaa | cgattacata | ggaggtataa | catgaagaaa | tttctgaaat | 300 |
| cgacagctgc | gcttgccctg | ggattatcgc | tgacgttcgg | gcttttcagc | cctgcccagg | 360 |
| ccatcacaag | tttgtacaaa | aaagcaggct | tcggcagcat | tgctcctaac | tttaaagtct | 420 |
| tgtcatggg | cccgcttgaa | aaagtcacag | attttaatgc | ctttaaagac | caacttatca | 480 |
| cgcttaaaaa | taatggtgtc | tatggcatta | caacggacat | ctggtgggc | tacgtcgaaa | 540 |
| acgccggtga | aaaccaattt | gactggagct | attataaaac | atacgcggat | acggtcaggg | 600 |
| ccgcgggtct | taaatgggtc | cctattatga | gcacgcatgc | gtgcggcggc | aacgtcggcg | 660 |
| atacagtcaa | catcccgatt | ccgagctggg | tctggacaaa | agatacacaa | gataacatgc | 720 |
| aatacaaaga | cgaagcaggc | aattgggaca | tgaagccgt | cagcccgtgg | tacagcggcc | 780 |
| ttacacagct | ttataacgaa | ttttatagca | gctttgccag | caactttagc | agctataaag | 840 |
| atatcatcac | aaaaatctat | attagcggcg | gccctagcgg | cgaacttagg | tatcctagct | 900 |
| acaatccttc | acatggctgg | acgtatcctg | gcaggggcag | ccttcagtgt | tatagcaaag | 960 |
| cggccatcac | atcatttcaa | aatgcgatga | aaagcaaata | tggcacgatc | gcggctgtca | 1020 |
| atagcgcatg | gggtacaagc | cttacagatt | ttagccagat | tagccctcct | acggacggcg | 1080 |
| ataactttt | tacaaacggc | tataaaacga | cgtatggtaa | tgatttttctt | acatggtatc | 1140 |
| agagcgtcct | tacaaatgaa | cttgcgaata | ttgctagcgt | cgctcatagc | tgctttgacc | 1200 |
| cggtctttaa | tgtcccgatt | ggcgcaaaaa | tcgcaggcgt | ccattggctt | tacaatagcc | 1260 |
| cgacaatgcc | gcatgcggca | gaatactgtg | cgggctacta | taattatagc | acgcttcttg | 1320 |
| accaatttaa | agctagcaac | cttgcgatga | catttacatg | ccttgaaatg | gatgatagca | 1380 |
| acgcctatgt | cagcccgtac | tacagcgcgc | cgatgacact | tgtccattat | gtcgcaaatc | 1440 |
| ttgccaataa | taaaggcatt | gtccataatg | gtgaaaatgc | acttgctatt | agcaacaata | 1500 |
| atcaagcgta | tgtcaactgc | gctaacgaac | ttacaggcta | taattttagc | ggctttacac | 1560 |
| ttcttaggct | tagcaacatt | gtcaatagcg | atggcagcgt | cacaagcgaa | atggcgccgt | 1620 |
| tgtcattaa | catcgtcacg | cttacaccga | acggcacgat | tcctgtcacg | tttacgatta | 1680 |
| acaacgcaac | aacatactat | ggccagaatg | tctacatcgt | cggcagcaca | agcgatcttg | 1740 |
| gcaattggaa | cacgacgtat | gccaggggcc | cggctagctg | ccctaattat | ccgacgtgga | 1800 |
| cgatcacact | taaccttctt | ccgggcgaac | aaatccagtt | taaagcggtc | aaaatcgata | 1860 |
| gcagcggcaa | tgtcacatgg | gaaggtggta | gcaaccatac | atacacagtc | ccgacgagcg | 1920 |
| gcacaggcag | cgtcacaatt | acgtggcaaa | accaccacca | ccaccaccac | taa | 1973 |

<210> SEQ ID NO 4
<211> LENGTH: 2000

<212> TYPE: DNA
<213> ORGANISM: Artificial Sequence
<220> FEATURE:
<223> OTHER INFORMATION: Synthetic construct

<400> SEQUENCE: 4

| | | | | | |
|---|---|---|---|---|---|
| ggccgcggtc | ctcgggatat | gataagatta | atagttttag | ctattaatct | tttttttattt | 60 |
| ttatttaaga | atggcttaat | aaagcggtta | ctttggattt | ttgtgagctt | ggactagaaa | 120 |
| aaaacttcac | aaaatgctat | actaggtagg | taaaaaaata | ttcggaggaa | ttttgaaatg | 180 |
| gcaatcgttt | cagcagaaaa | attcgtaatt | cgagctcgcc | cccggggatc | cggcgacagc | 240 |
| ggacaagcct | ggaattcaaa | cgattacata | ggaggtataa | catgagattc | gagtacctgc | 300 |
| gccagaacgt | tgtcggtttg | gctctttcta | ccgccctgat | cgcatccctc | agcggccctg | 360 |
| cttttgccca | acacgacgct | aatgctgcca | tcacaagttt | gtacaaaaaa | gcaggcttcg | 420 |
| gcagcattgc | tcctaacttt | aaagtctttg | tcatgggccc | gcttgaaaaa | gtcacagatt | 480 |
| ttaatgcctt | taaagaccaa | cttatcacgc | ttaaaaataa | tggtgtctat | ggcattacaa | 540 |
| cggacatctg | gtggggctac | gtcgaaaacg | ccggtgaaaa | ccaatttgac | tggagctatt | 600 |
| ataaaacata | cgcggatacg | gtcagggccg | cgggtcttaa | atgggtccct | attatgagca | 660 |
| cgcatgcgtg | cggcggcaac | gtcggcgata | cagtcaacat | cccgattccg | agctgggtct | 720 |
| ggacaaaaga | tacacaagat | aacatgcaat | acaaagacga | agcaggcaat | gggacaatg | 780 |
| aagccgtcag | cccgtggtac | agcggcctta | cacagcttta | taacgaattt | tatagcagct | 840 |
| ttgccagcaa | ctttagcagc | tataaagata | tcatcacaaa | aatctatatt | agcggcggcc | 900 |
| ctagcggcga | acttaggtat | cctagctaca | atccttcaca | tggctggacg | tatcctggca | 960 |
| ggggcagcct | tcagtgttat | agcaaagcgg | ccatcacatc | atttcaaaat | gcgatgaaaa | 1020 |
| gcaaatatgg | cacgatcgcg | gctgtcaata | gcgcatgggg | tacaagcctt | acagatttta | 1080 |
| gccagattag | ccctcctacg | gacggcgata | acttttttac | aaacggctat | aaaacgacgt | 1140 |
| atggtaatga | ttttcttaca | tggtatcaga | gcgtccttac | aaatgaactt | gcgaatattg | 1200 |
| ctagcgtcgc | tcatagctgc | tttgacccgg | tctttaatgt | cccgattggc | gcaaaaatcg | 1260 |
| caggcgtcca | ttggctttac | aatagcccga | caatgccgca | tgcggcagaa | tactgtgcgg | 1320 |
| gctactataa | ttatagcacg | cttcttgacc | aatttaaagc | tagcaacctt | gcgatgacat | 1380 |
| ttacatgcct | tgaaatggat | gatagcaacg | cctatgtcag | cccgtactac | agcgcgccga | 1440 |
| tgacacttgt | ccattatgtc | gcaaatcttg | ccaataataa | aggcattgtc | cataatggtg | 1500 |
| aaaatgcact | tgctattagc | aacaataatc | aagcgtatgt | caactgcgct | aacgaactta | 1560 |
| caggctataa | ttttagcggc | tttacacttc | ttaggcttag | caacattgtc | aatagcgatg | 1620 |
| gcagcgtcac | aagcgaaatg | gcgccgtttg | tcattaacat | cgtcacgctt | acaccgaacg | 1680 |
| gcacgattcc | tgtcacgttt | acgattaaca | acgcaacaac | atactatggc | cagaatgtct | 1740 |
| acatcgtcgg | cagcacaagc | gatcttggca | attggaacac | gacgtatgcc | aggggcccgg | 1800 |
| ctagctgccc | taattatccg | acgtggacga | tcacacttaa | ccttcttccg | ggcgaacaaa | 1860 |
| tccagtttaa | agcggtcaaa | atcgatagca | gcggcaatgt | cacatgggaa | ggtggtagca | 1920 |
| accatacata | cacagtcccg | acgagcggca | caggcagcgt | cacaattacg | tggcaaaacc | 1980 |
| accaccacca | ccaccactaa | | | | | 2000 |

<210> SEQ ID NO 5
<211> LENGTH: 572
<212> TYPE: PRT

<213> ORGANISM: Pseudogluconobacter saccharoketogenes

<400> SEQUENCE: 5

```
Ala Glu Pro Ser Lys Ala Gly Gln Ser Ala Ile Glu Asn Phe Gln Pro
1               5                   10                  15

Val Thr Ala Asp Asp Leu Ala Gly Lys Asn Pro Ala Asn Trp Pro Ile
            20                  25                  30

Leu Arg Gly Asn Tyr Gln Gly Trp Gly Tyr Ser Pro Leu Asp Gln Ile
        35                  40                  45

Asn Lys Asp Asn Val Gly Asp Leu Gln Leu Val Trp Ser Arg Thr Met
    50                  55                  60

Glu Pro Gly Ser Asn Glu Gly Ala Ala Ile Ala Tyr Asn Gly Val Ile
65                  70                  75                  80

Phe Leu Gly Asn Thr Asn Asp Val Ile Gln Ala Ile Asp Gly Lys Thr
                85                  90                  95

Gly Ser Leu Ile Trp Glu Tyr Arg Arg Lys Leu Pro Ser Ala Ser Lys
            100                 105                 110

Phe Ile Asn Ser Leu Gly Ala Ala Lys Arg Ser Ile Ala Leu Phe Gly
        115                 120                 125

Asp Lys Val Tyr Phe Val Ser Trp Asp Asn Phe Val Val Ala Leu Asp
    130                 135                 140

Ala Lys Thr Gly Lys Leu Ala Trp Glu Thr Asn Arg Gly Gln Gly Val
145                 150                 155                 160

Glu Glu Gly Val Ala Asn Ser Ser Gly Pro Ile Val Val Asp Gly Val
                165                 170                 175

Val Ile Ala Gly Ser Thr Cys Gln Phe Ser Gly Phe Cys Tyr Val
            180                 185                 190

Thr Gly Thr Asp Ala Glu Ser Gly Glu Glu Leu Trp Arg Asn Thr Phe
        195                 200                 205

Ile Pro Arg Pro Gly Glu Glu Gly Asp Asp Thr Trp Gly Gly Ala Pro
    210                 215                 220

Tyr Glu Asn Arg Trp Met Thr Gly Ala Trp Gly Gln Ile Thr Tyr Asp
225                 230                 235                 240

Pro Glu Leu Asp Leu Val Tyr Tyr Gly Ser Thr Gly Ala Gly Pro Ala
                245                 250                 255

Ser Glu Val Gln Arg Gly Thr Glu Gly Gly Thr Leu Ala Gly Thr Asn
            260                 265                 270

Thr Arg Phe Ala Val Lys Pro Lys Thr Gly Glu Val Val Trp Lys His
        275                 280                 285

Gln Thr Leu Pro Arg Asp Asn Trp Asp Ser Glu Cys Thr Phe Glu Met
    290                 295                 300

Met Val Ser Thr Ser Val Asn Pro Asp Ala Lys Ala Asp Gly Met
305                 310                 315                 320

Met Ser Val Gly Ala Asn Val Pro Arg Gly Glu Thr Arg Lys Val Leu
                325                 330                 335

Thr Gly Val Pro Cys Lys Thr Gly Val Ala Trp Gln Phe Asp Ala Lys
            340                 345                 350

Thr Gly Asp Tyr Phe Trp Ser Lys Ala Thr Val Glu Gln Asn Ser Ile
        355                 360                 365

Ala Ser Ile Asp Asp Thr Gly Leu Val Thr Val Asn Glu Asp Met Ile
    370                 375                 380

Leu Lys Glu Pro Gly Lys Thr Tyr Asn Tyr Cys Pro Thr Phe Leu Gly
385                 390                 395                 400
```

```
Gly Arg Asp Trp Pro Ser Ala Gly Tyr Leu Pro Lys Ser Asn Leu Tyr
            405                 410                 415
Val Ile Pro Leu Ser Asn Ala Cys Tyr Asp Val Met Ala Arg Thr Thr
        420                 425                 430
Glu Ala Thr Pro Ala Asp Val Tyr Asn Thr Asp Ala Thr Leu Val Leu
    435                 440                 445
Ala Pro Gly Lys Thr Asn Met Gly Arg Val Asp Ala Ile Asp Leu Ala
450                 455                 460
Thr Gly Glu Thr Lys Trp Ser Tyr Glu Thr Arg Ala Ala Leu Tyr Asp
465                 470                 475                 480
Pro Val Leu Thr Thr Gly Gly Asp Leu Val Phe Val Gly Gly Ile Asp
            485                 490                 495
Arg Asp Phe Arg Ala Leu Asp Ala Glu Ser Gly Lys Glu Val Trp Ser
        500                 505                 510
Thr Arg Leu Pro Gly Ala Val Ser Gly Tyr Thr Thr Ser Tyr Ser Ile
    515                 520                 525
Asp Gly Arg Gln Tyr Val Ala Val Val Ser Gly Ser Leu Gly Gly
530                 535                 540
Pro Thr Phe Gly Pro Thr Thr Pro Asp Val Asp Ser Ala Ser Gly Ala
545                 550                 555                 560
Asn Gly Ile Tyr Val Phe Ala Leu Pro Glu Lys Lys
            565                 570
```

```
<210> SEQ ID NO 6
<211> LENGTH: 36
<212> TYPE: PRT
<213> ORGANISM: Pseudogluconobacter saccharoketogenes

<400> SEQUENCE: 6

Met Arg Phe Glu Tyr Leu Arg Gln Asn Val Val Gly Leu Ala Leu Ser
1               5                   10                  15
Thr Ala Leu Ile Ala Ser Leu Ser Gly Pro Ala Phe Ala Gln His Asp
            20                  25                  30
Ala Asn Ala Ala
        35

<210> SEQ ID NO 7
<211> LENGTH: 4
<212> TYPE: PRT
<213> ORGANISM: Artificial Sequence
<220> FEATURE:
<223> OTHER INFORMATION: Peptide sequence

<400> SEQUENCE: 7

Ala Glu Pro Ser
1

<210> SEQ ID NO 8
<211> LENGTH: 10
<212> TYPE: PRT
<213> ORGANISM: Artificial Sequence
<220> FEATURE:
<223> OTHER INFORMATION: Peptide sequence

<400> SEQUENCE: 8

Ala Glu Pro Ser Lys Ala Gly Gln Ser Ala
1               5                   10

<210> SEQ ID NO 9
<211> LENGTH: 70
```

```
<212> TYPE: PRT
<213> ORGANISM: Pseudogluconobacter saccharoketogenes

<400> SEQUENCE: 9

Met Arg Phe Glu Tyr Leu Arg Gln Asn Val Val Gly Leu Ala Leu Ser
1               5                   10                  15

Thr Ala Leu Ile Ala Ser Leu Ser Gly Pro Ala Phe Ala Gln His Asp
            20                  25                  30

Ala Asn Ala Ala Ala Glu Pro Ser Lys Ala Gly Gln Ser Ala Ile Glu
        35                  40                  45

Asn Phe Gln Pro Val Thr Ala Asp Asp Leu Ala Gly Lys Asn Pro Ala
    50                  55                  60

Asn Trp Pro Ile Leu Arg
65                  70
```